United States Patent
Watanabe et al.

(10) Patent No.: US 10,908,120 B2
(45) Date of Patent: Feb. 2, 2021

(54) SEMICONDUCTOR BIOSENSOR AND CONTROL METHOD THEREOF

(71) Applicant: Laurus Corporation, Tokyo (JP)

(72) Inventors: Hiroshi Watanabe, Kanagawa-ken (JP); Zhe-An Lee, Hsinchu (TW); Ikuo Kurachi, Tokyo (JP)

(73) Assignee: Laurus Corporation, Tokyo (JP)

( * ) Notice: Subject to any disclaimer, the term of this patent is extended or adjusted under 35 U.S.C. 154(b) by 15 days.

(21) Appl. No.: 16/257,445

(22) Filed: Jan. 25, 2019

(65) Prior Publication Data

US 2019/0154631 A1 May 23, 2019

Related U.S. Application Data

(63) Continuation-in-part of application No. 14/792,661, filed on Jul. 7, 2015, now abandoned.

(30) Foreign Application Priority Data

Aug. 7, 2014 (JP) ................................. 2014-169886

(51) Int. Cl.
 *G01N 27/414* (2006.01)
 *G01N 33/543* (2006.01)
 *G01N 27/327* (2006.01)

(52) U.S. Cl.
 CPC ..... *G01N 27/4145* (2013.01); *G01N 33/5438* (2013.01); *G01N 27/3272* (2013.01)

(58) Field of Classification Search
 CPC ........... G01N 27/4145; G01N 27/3272; G01N 33/5438
 See application file for complete search history.

(56) References Cited

U.S. PATENT DOCUMENTS

| | | |
|---|---|---|
| 4,743,954 A | 5/1988 | Brown |
| 5,031,145 A | 7/1991 | Lever |
| | (Continued) | |

FOREIGN PATENT DOCUMENTS

EP  0969282 A2  1/2000

OTHER PUBLICATIONS

Tomoharu Tanaka et al., A 4-Mbit NAND-EEPROM with Tight Programmed Vt Distribution. 1990 Symposium on VLSI Circuits, 1990, pp. 105-106, IEEE, Japan.

(Continued)

*Primary Examiner* — Robert J Eom
(74) *Attorney, Agent, or Firm* — Alan D. Kamrath; Karin L. Williams; Mayer & Williams PC

(57) ABSTRACT

A semiconductor biosensor includes a central reaction unit of an inspection equipment. The central reaction unit includes a plurality of first conducting wires, a plurality of second conducting wires, a common electrode source, a plurality of sense-amplifiers, a plurality of non-volatile memory type transistors, and a first oxide film. Each sense-amplifier is connected to a respective second conducting wire. The non-volatile memory type transistors are respectively formed on the second conducting wires. Each non-volatile memory type transistor includes a control gate, a third oxide film, a floating gate, and a second oxide. The first oxide film wraps or covers the first conducting wires. Receptors are fixed on a surface of the first oxide film. A portion of the targets couples with a portion of the receptors to form composite bodies. The sense-amplifiers are configured to detect a change in a current signal based on the charges of the composite bodies.

8 Claims, 35 Drawing Sheets

(56) References Cited

U.S. PATENT DOCUMENTS

| 6,280,557 | B1 | 8/2001 | Matsumoto |
| 7,885,697 | B2 | 2/2011 | Brister et al. |
| 8,052,931 | B2 | 11/2011 | Bansal et al. |
| 2006/0020186 | A1 | 1/2006 | Brister et al. |
| 2010/0039126 | A1 | 2/2010 | Chen |
| 2011/0163812 | A1 | 7/2011 | Bansal et al. |
| 2013/0143221 | A1 | 6/2013 | Beauchemin |

OTHER PUBLICATIONS

Reed, Mark A., "CMOS biosensor devices and applications", Electron Devices Meeting (IEDM), 2013 IEEE International, IEEE, 2013.

Kazuto Koike et al., A Potentiometric Immunosensor Based on a ZnO Field-effect Transistor, Japanese Journal of Applied Physics (Regular Paper), 2014, 5 pages, vol. 53 issue 05FF04, published online iopscience.iop.org.

SEMICONDUCTOR BIOSENSOR AND CONTROL METHOD THEREOF

CROSS REFERENCE TO RELATED APPLICATIONS

This is a continuation-in-part application of U.S. patent application Ser. No. 14/792,661 filed on Jul. 7, 2015.

The application claims the benefit of Japanese patent application serial No. 2014-169886, filed on Aug. 7, 2014, and the entire contents of which are incorporated herein by reference.

FIELD OF THE INVENTION

The present invention relates to a semiconductor biosensor which is used for healthcare chip and a control method of the semiconductor biosensor.

DESCRIPTION OF THE RELATED ART

In recent years, it has become significant to suppress the drastic increase of medical expense since the society is aging in developed countries. It may be possible to find diseases early and thereby reduce the medical expense if it is possible to inspect and detect a little amount of chemical substance contained in a sample with high precision. It is expected that such an inspect method can be achieved by utilizing microelectronics technologies. (See K. Koike, et al., Jpn. J. Appl. Phys., vol. 53, 05FF04 (2014).)

However, the inspection equipment with high precision is not only expensive but also large in size. Thus, the inspection can only be carried out in large hospitals or medical facilities. This makes the inspection expensive, and the inspection period is often more than several days.

In other words, small inspection equipment with high precision may enable a small-scale medical institute to perform cheap inspection. The inspection period shall be substantially reduced with a simplified process of inspection, then substantially reducing the cost and improving the convenience of the inspection. Therefore, in order to cut the cost of the inspection, it is necessary to substantially reduce the size of inspection equipment while keeping the precision by utilizing the combined technologies of semiconductor micro-devices and biosensors.

FIG. 1 is an exemplary illustration of a basic device structure of a conventional semiconductor biosensor (See K. Koike, et al., Jpn. J. Appl. Phys., vol. 53, 05FF04 (2014).). An oxide film 1, a source electrode 2 and a drain electrode 3 are arranged on a semiconductor substrate 4. Those electrodes are covered by a resist film 100 to be protected from a solution (e.g.: a specimen such as blood, urine, sweat, and so forth) in which the inspection target is dissociated. This conventional semiconductor biosensor is exposed into the solution during inspection.

Referring to FIG. 10, in the solution, a target 7 and a receptor 8 are attached to the surface of the oxide film 1 to produce a chemical reaction. The chemical reaction normally has a dissociation constant 300 (K) for determining the equilibrium state thereof. When the dissociation constant 300 is larger, the decoupling prevails in the chemical reaction. To the contrary, when the dissociation constant 300 is smaller, the coupling prevails in the chemical reaction, and, thus, a composite body 5 is made on the surface of the oxide film 1, as illustrated FIGS. 2, 3, and 4.

The composite body 5 has a charge carried by the target 7. The charge will modulate a surface electric field of the semiconductor substrate 4. It may be capable of detecting whether the target 7 is contained in the solution by reading the change in electric current flowing between the source electrode 2 and the drain electrode 3.

There are many composite bodies 5 on the surface of the oxide film 1, as illustrated in FIG. 2, as long as the dissociation constant 300 is small. If the dissociation constant 300 is larger, the density of the composite bodies 5 is decreased, as illustrated in FIGS. 3 and 4.

Besides, if the number of the target 7 is more in solution, then, more composite bodies 5 are attached to the surface of the oxide film 1, as illustrated in FIG. 2. If the number of the target 7 is less in solution, then, as illustrated in FIGS. 3 and 4, the number of composite bodies 5 attached to the surface of the oxide film 1 becomes less.

The dissociation constant 300 is sensitive to the density of the target 7 in the solution and to the temperature.

In FIGS. 3, and 4, those charges of the composite bodies 5 are sparse on the surface of the oxide film 1 and work as point charges. In this regard, electrons flowing from the source electrode 2 to the drain electrode 3 can easily circumvent around the composite bodies 5, as shown in FIG. 6. Thereby, if the electrons flowing from the source electrode 2 to the drain electrode 3 along a roundabout route, those composite bodies 5 exhibit no impact on the electric current characteristics of the conventional semiconductor biosensor.

Therefore, referring to FIG. 7, another conventional semiconductor biosensor replaces the semiconductor substrate 4 with a wide gate width with a conducting wire 6 with a narrow gate width. Since electrons cannot circumvent around a composite body 5 while flowing through the conducting wire 6, there is no roundabout route for the electrons flowing from the source electrode 2 to the drain electrode 3. Thus, the transport speed of those electrons is reduced in average, and the electric current is suppressed. In theory, it may be possible to detect a sole target 7 as long as the change in the electric current can be sensed.

In general, the change in electric current ($\Delta I_{ds}$) flowing on the semiconductor surface of transistors is sensed as a change in threshold voltage shift ($\Delta V_t$). Depicting the transconductance $g_m$, the surface density of the total charge $Q_x$ carried by the target 7, the gate capacitance of the transistor C, the surface density of the receptors 8 [Y], the density of the target 7 in solution [X], formula 1 is obtained with the cut-off to the background noise:

$$\frac{\Delta I_{ds}}{g_m} = \Delta V_t = \frac{Q_X}{C}[Y] \times \frac{[X]}{[X]+K} + \text{(cut-off)} \qquad \text{[Formula 1]}$$

The cut-off is predetermined for veiling the noise not related to biosensors and must be much smaller than any noise attributable to the biosensors.

According to Formula 1, the limit of detection (LOD) is obtained as formula 2, where $I_{noise}$ is the absolute value of the electric current caused by the noise attributable to the biosensors. (See M. A. Reed, IEEE IEDM13, pp. 208-211 (2013).)

$$LOD = \frac{K}{\left(\frac{Q_X[Y]/C}{I_{noise}/g_m - \text{(cut-off)}}\right)} \qquad \text{[Formula 2]}$$

According to Formula 2, it is found that LOD is made small as long as $I_{noise}$ becomes small and is equal to the cut-off.

As mentioned above, $I_{noise}$ can be made small by using the conducting wires 6 to replace the semiconductor substrate 4. Specifically, referring to FIG. 5, there are a plurality of conducting wires 6 in parallel between a common source 2 and a common drain 3. As an example, there are three conducting wires 6, each of which can detect a sole composite body 5 on the surface of the oxide film 1. Then, it appears that the LOD is made small.

However, all of the conducting wires 6 are connected to the common drain 3, which indicates that the current signals from the conducting wires 6 are added. Once the signals are added up, it is impossible to distinguish signals from different conducting wires 6. Therefore, the LOD is not improved significantly.

SUMMARY OF THE INVENTION

An objective of the present disclosure is to provide a semiconductor biosensor and a control method thereof with improved limit of detection.

In an aspect, a semiconductor biosensor including a central reaction unit of an inspection equipment is disclosed. The central reaction unit includes a plurality of first conducting wires, a plurality of second conducting wires, a common electrode source, a plurality of sense-amplifiers, a plurality of non-volatile memory type transistors, and a first oxide film. An end of each of the plurality of first conducting wires is connected to the common electrode source. Another end of each of the plurality of first conducting wires is connected to an end of a respective one of the plurality of second conducting wires. Each of the plurality of sense-amplifiers is electrically connected to another end of the respective one of the plurality of second conducting wires. The plurality of non-volatile memory type transistors is respectively formed on the plurality of second conducting wires. Each of the plurality of non-volatile memory type transistors includes a control gate connecting to a corresponding one of the plurality of sense-amplifiers, a third oxide film, a floating gate, and a second oxide film formed below the floating gate and on a corresponding one of the plurality of second conducting wires. The first oxide film wraps or covers the plurality of first conducting wires. A plurality of receptors is fixed on a surface of the first oxide film but not on a surface of the second oxide film. A portion of the plurality of targets couples with a portion of the plurality of receptors to form a plurality of composite bodies. The plurality of first conducting wires, the first oxide film and the plurality of receptors jointly delimit a first part of the central reaction unit, and the plurality of second conducting wires and the plurality of non-volatile memory type transistors jointly delimit a second part of the central reaction unit. None of the plurality of second conducting wires and none of the plurality of non-volatile memory type transistors are within the first part. The plurality of sense-amplifiers is configured to detect a change in a current signal based on charges of the plurality of composite bodies. An improving factor ε of a limit of detection (LOD) of the plurality of sense-amplifiers is defined as:

$$\varepsilon \cong 1 - \frac{m}{M}.$$

M is a total number of the plurality of sense-amplifiers. m is a sum of a number of the plurality of sense-amplifiers which detects one of the plurality of composite bodies and a number of the plurality of sense-amplifiers which are contaminated with noise. An improved limit of detection (LOD) of the plurality of sense-amplifiers is defined as:

Improved LOD=(1−ε)×LOD=$m/M$×LOD.

The semiconductor biosensor is configured to adjust the improving factor ε of the plurality of sense-amplifiers to obtain the improved limit of detection by tuning M and m.

A control method of the semiconductor biosensor includes providing the above semiconductor biosensor, initializing the semiconductor biosensor by independently sensing output signals from the plurality of second conducting wires by the plurality of sense-amplifiers while a read voltage is applied to the control gates, testing the plurality of first conducting wires for wire-errors in which a portion of the plurality of first conducting wires with anomalously high resistance or which is snapped is regarded as first conducting wires having said wire-errors, data-thinning the semiconductor biosensor by selectively applying a program voltage to program one or more of the plurality of non-volatile memory type transistors respectively connected to one or more of the plurality of first conducting wires having said wire-errors to electrically disconnect each of the one or more of the plurality of first conducting wires having said wire-errors from a respective one of the plurality of sense-amplifiers, exposing the semiconductor biosensor into the solution dissociating the plurality of targets in which the plurality of targets moves in the solution, and detecting a change in the current signal output from one of the plurality of first conducting wires without said wire-errors based on the charges of the plurality of composite bodies.

In accordance to the above structure and method, it is capable of producing a central reaction unit as a key device of the semiconductor biosensor to achieve highly-precise and very small inspection equipment.

Embodiments according to the present invention will be explained below with reference to the drawings. These embodiments are not intended to limit the present invention. The drawings schematically show practical devices and are not made to scale.

BRIEF DESCRIPTION OF THE DRAWINGS

The illustrative embodiments may best be described by reference to the accompanying drawings where.

DETAILED DESCRIPTION OF THE INVENTION

Figure 8:
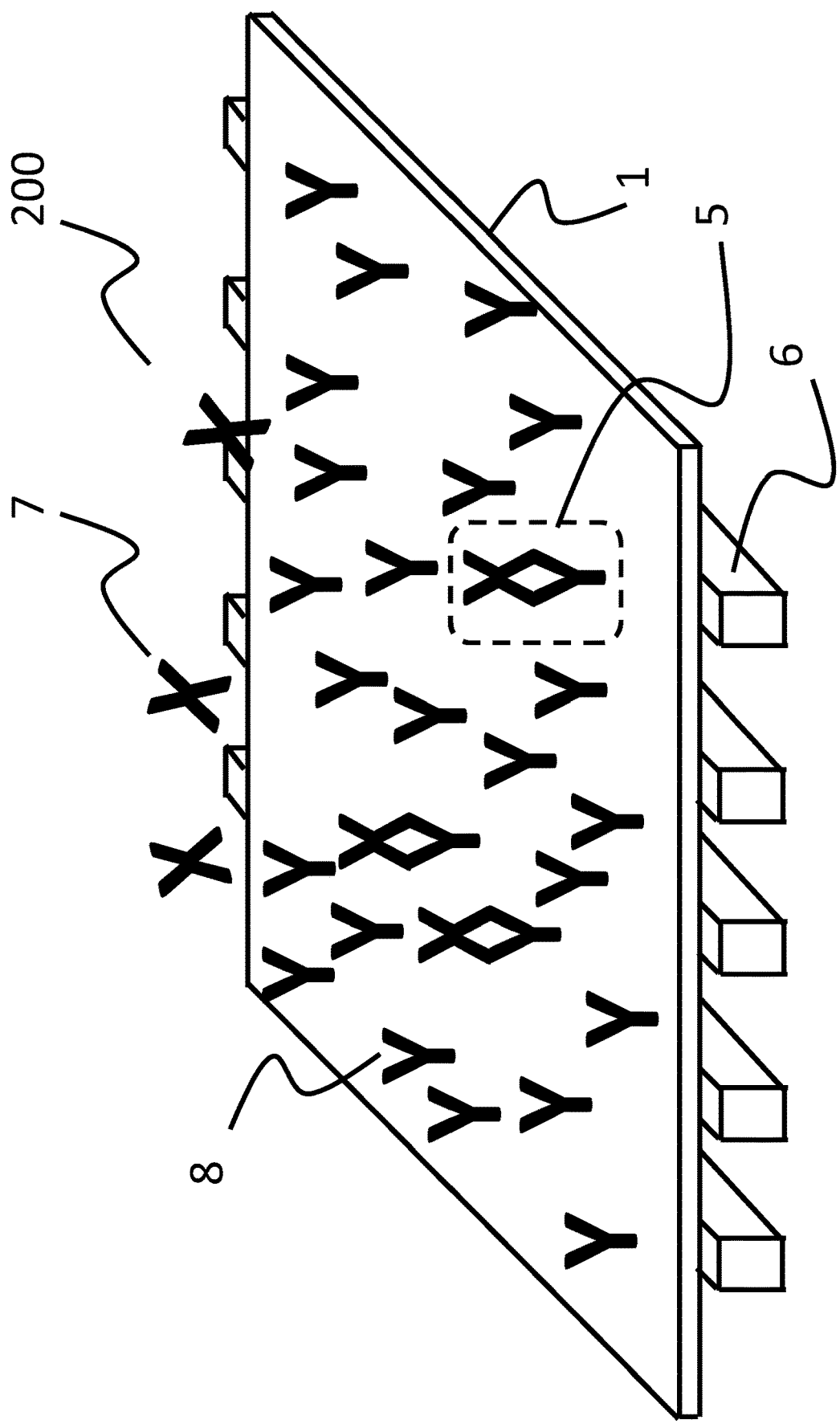
FIG. 8 is a view illustrating that receptors are attached on an oxide surface and that targets moving in solution are caught by those receptors and immobilized.

Referring to FIG. 8, an embodiment of the semiconductor biosensor related to the present invention is constituted of a central reaction unit 200 comprising conducting wires 6, an oxide film 1, receptors 8, and the peripheral unit described below. The conducting wires 6 can be thin conducting wires. Moreover, the conducting wires 6 can be nanowires.

Figure 10:
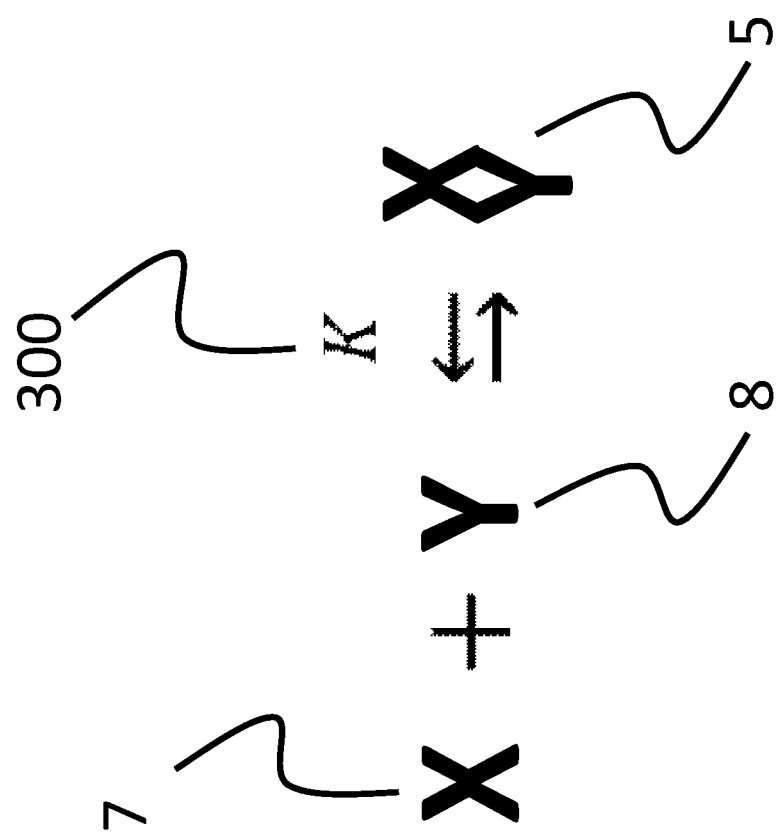
FIG. 10 is a view illustrating a reaction of receptors and, targets, which is related to an embodiment of the present invention.

The central reaction unit 200 is fabricated on the semiconductor substrate. The central reaction unit 200 is exposed into a solution dissociating targets 7. The targets 7 have a charge moving in the solution and then couple with the receptors 8 attached to the surface of the oxide film 1 subject to the formula shown in FIG. 10. The dissociation constant 300 determines the equilibrium state of the chemical reaction of the targets 7 and the receptors 8. When K is large, then the receptors 8 and the targets 7 are decoupled. When K is small, then the receptors 8 and the targets 7 are coupled to form immobilized composite bodies 5.

Figure 9:
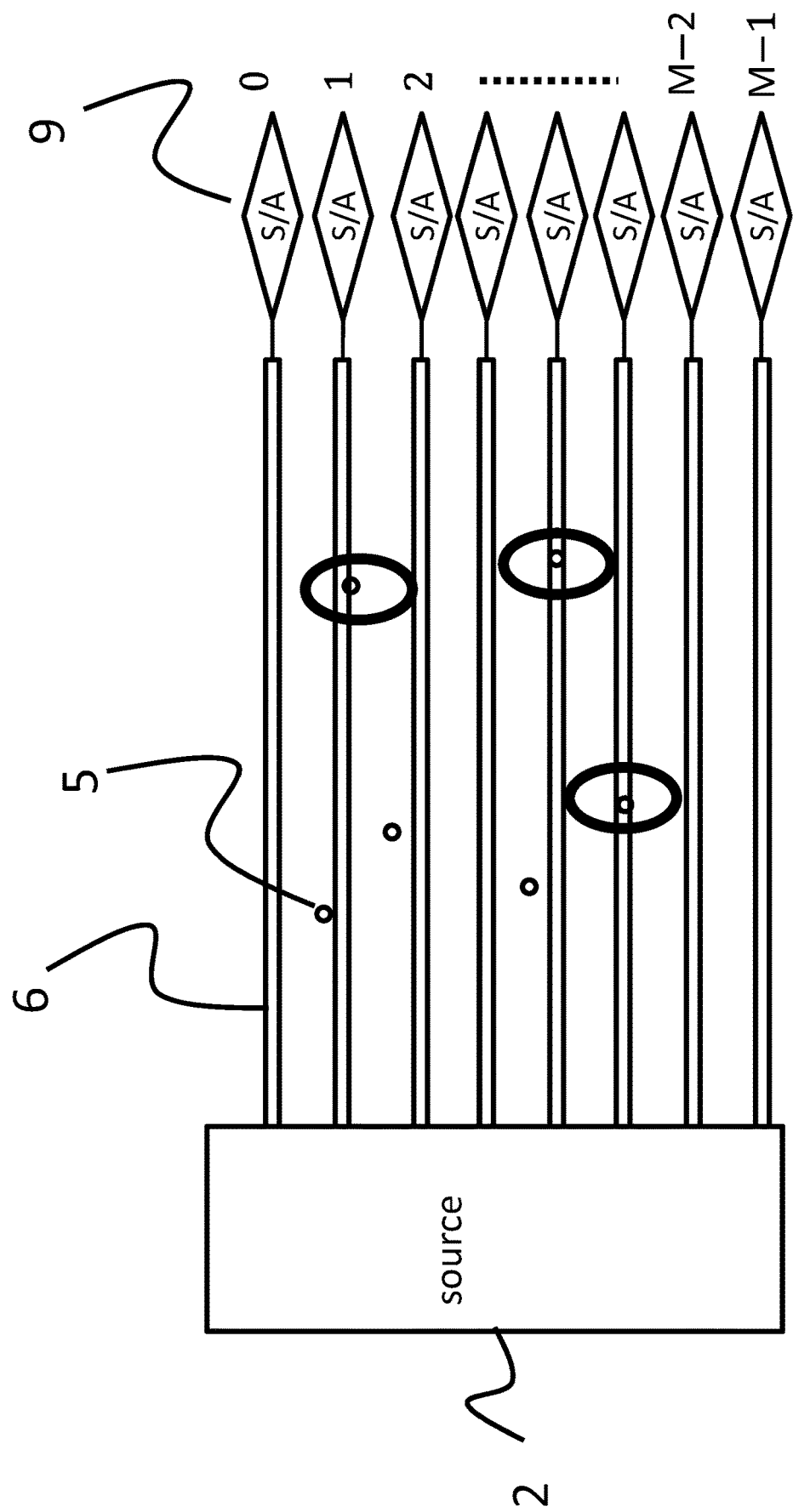
FIG. 9 is a view illustrating a basic component related to an embodiment of the present invention.

Referring to FIG. 9, the central reaction unit 200 further comprises a plurality of sense-amplifiers 9 (S/A). One end of each conducting wire 6 is connected to a common source 2, and another end of each conducting wire 6 is connected to each sense-amplifier 9. The number of the sense-amplifiers (M) is the same with the number of the conducting wires 6, and the sense-amplifiers 9 are labeled from 0 to M−1, respectively.

Figure 1:
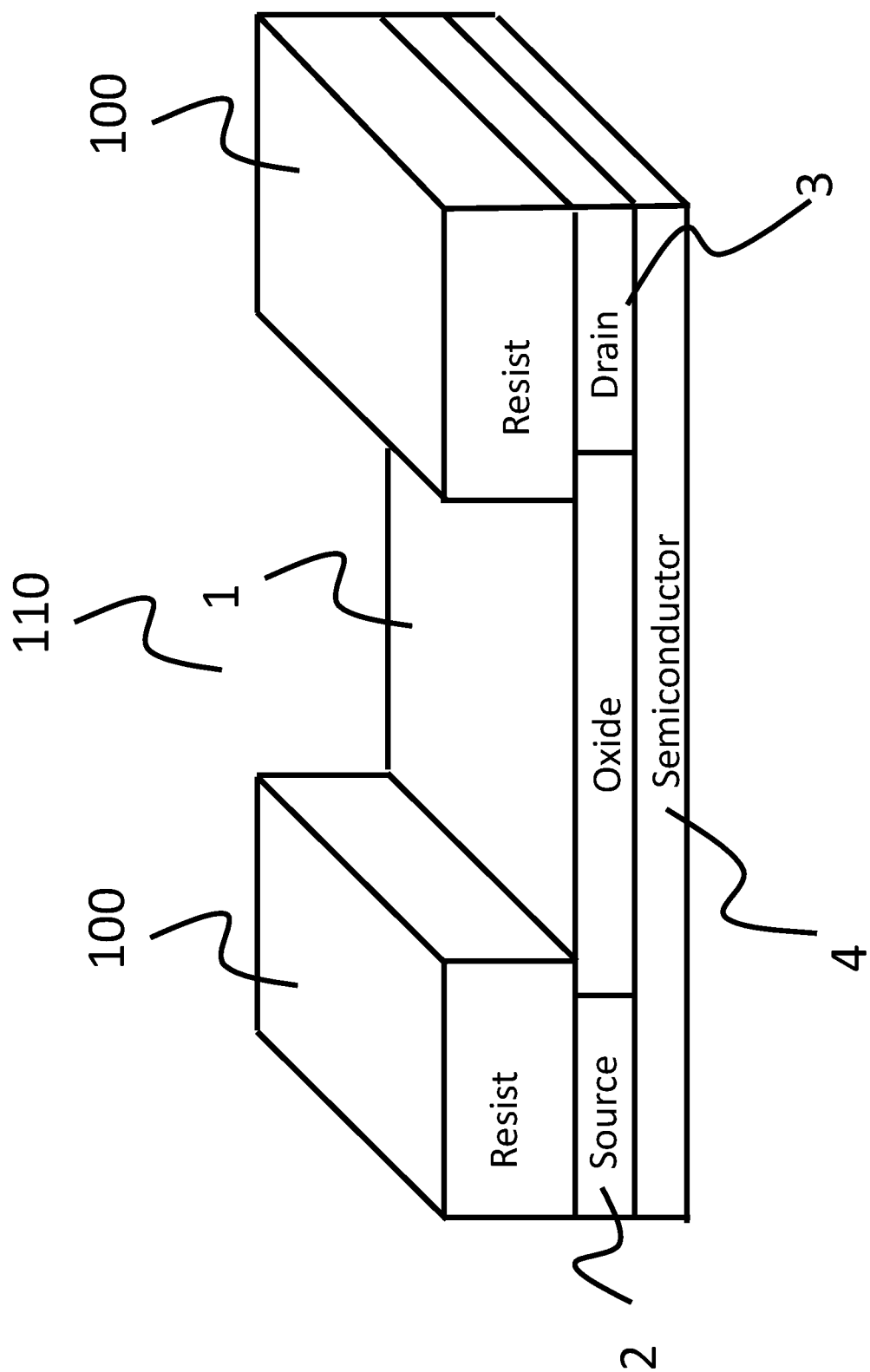
FIG. 1 is a view illustrating a basic device structure of a prior art biosensor.
Figure 2:
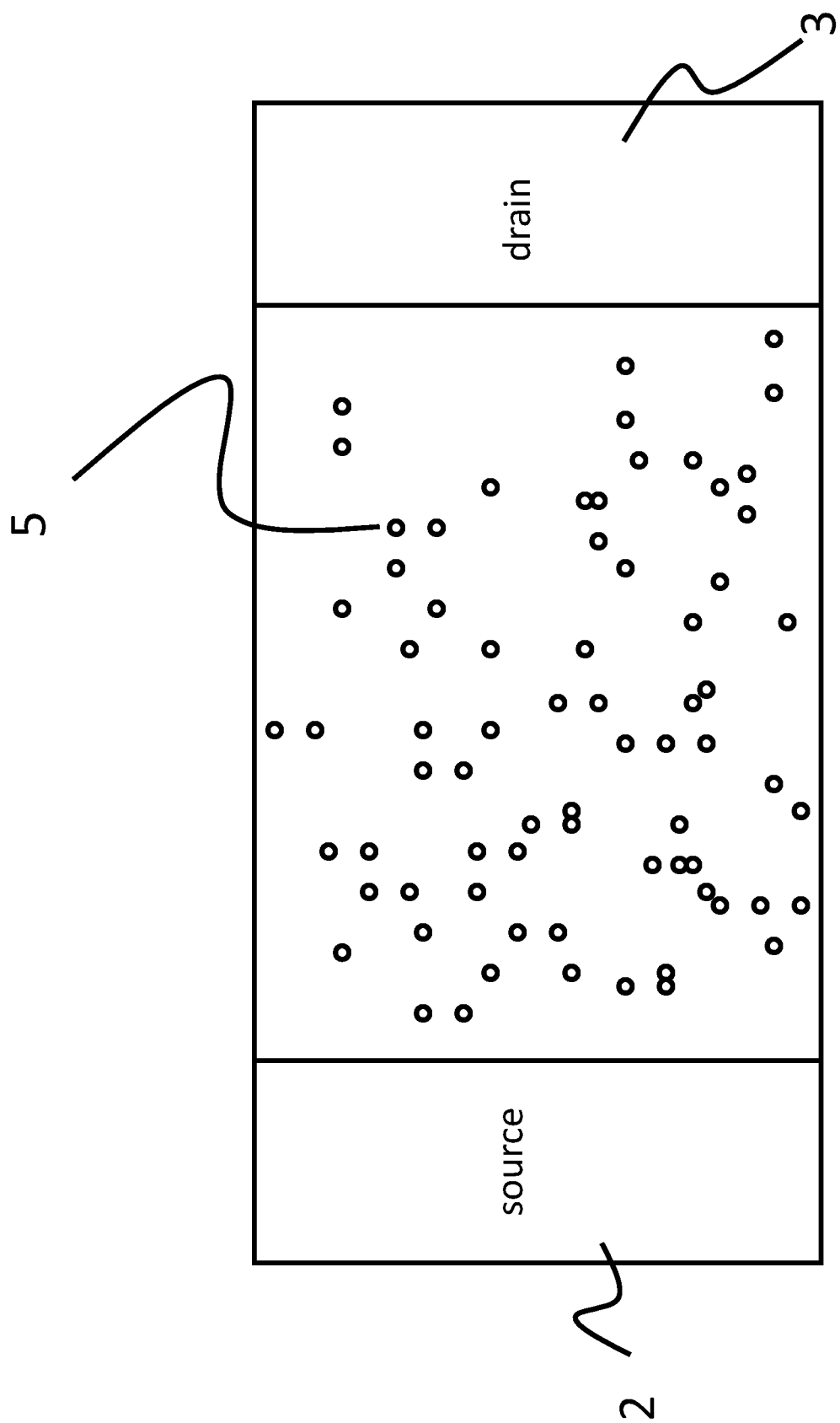
FIG. 2 is a view illustrating a basic device structure of a prior art biosensor.
Figure 3:
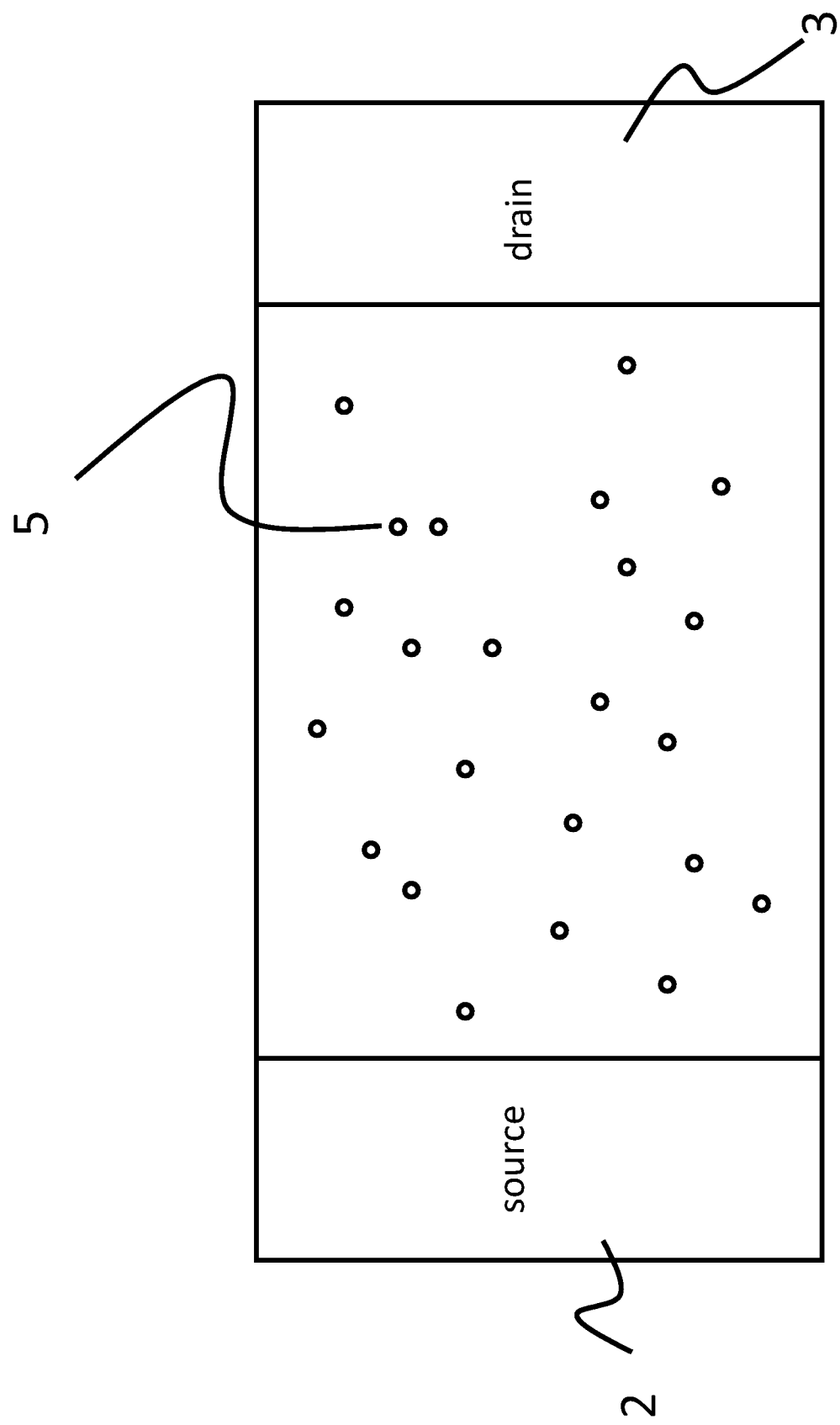
FIG. 3 is a view illustrating a basic device structure of a prior art biosensor.
Figure 4:
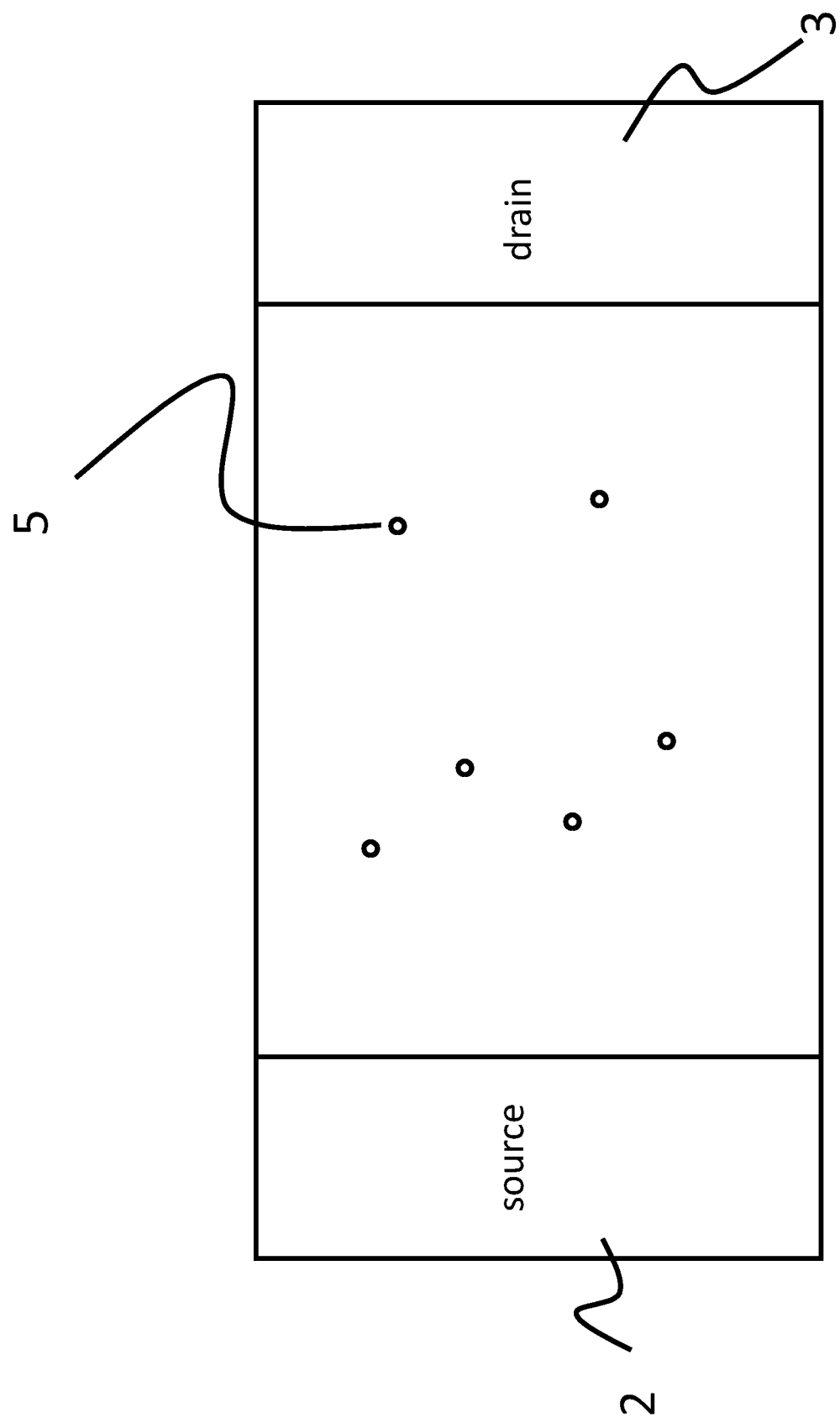
FIG. 4 is a view illustrating a basic device structure of a prior art biosensor.
Figure 5:
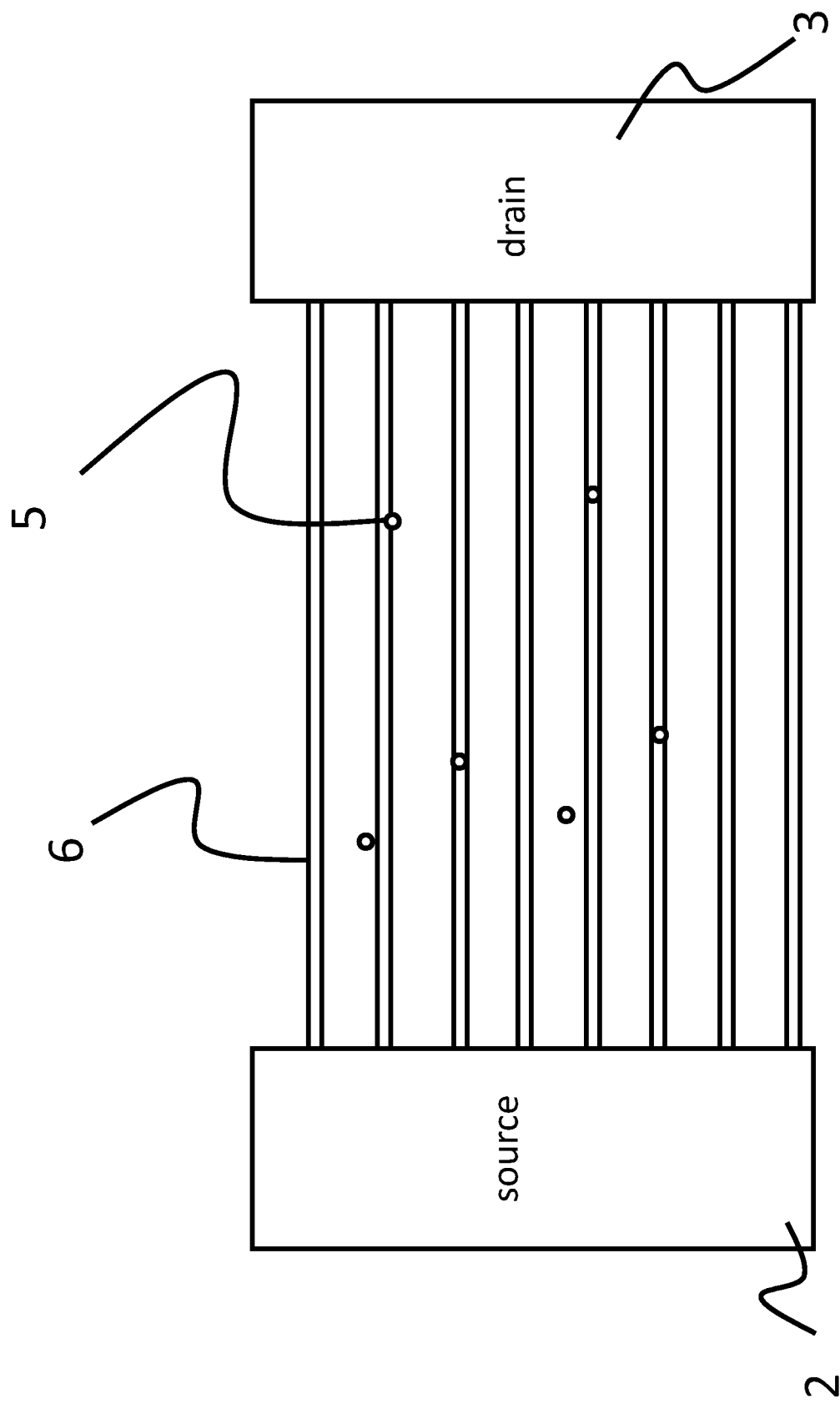
FIG. 5 is a view illustrating a basic device structure of a prior art biosensor.
Figure 6:
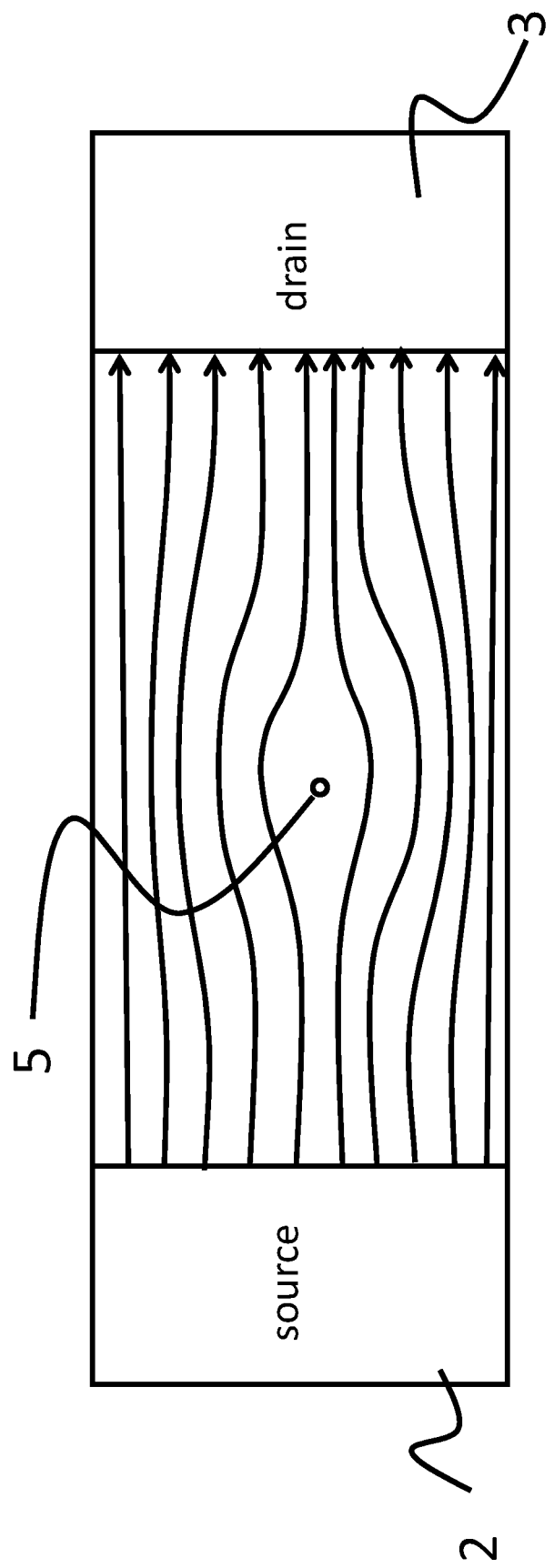
FIG. 6 is a view illustrating that electrons flow around a charge in the prior art biosensor.
Figure 7:
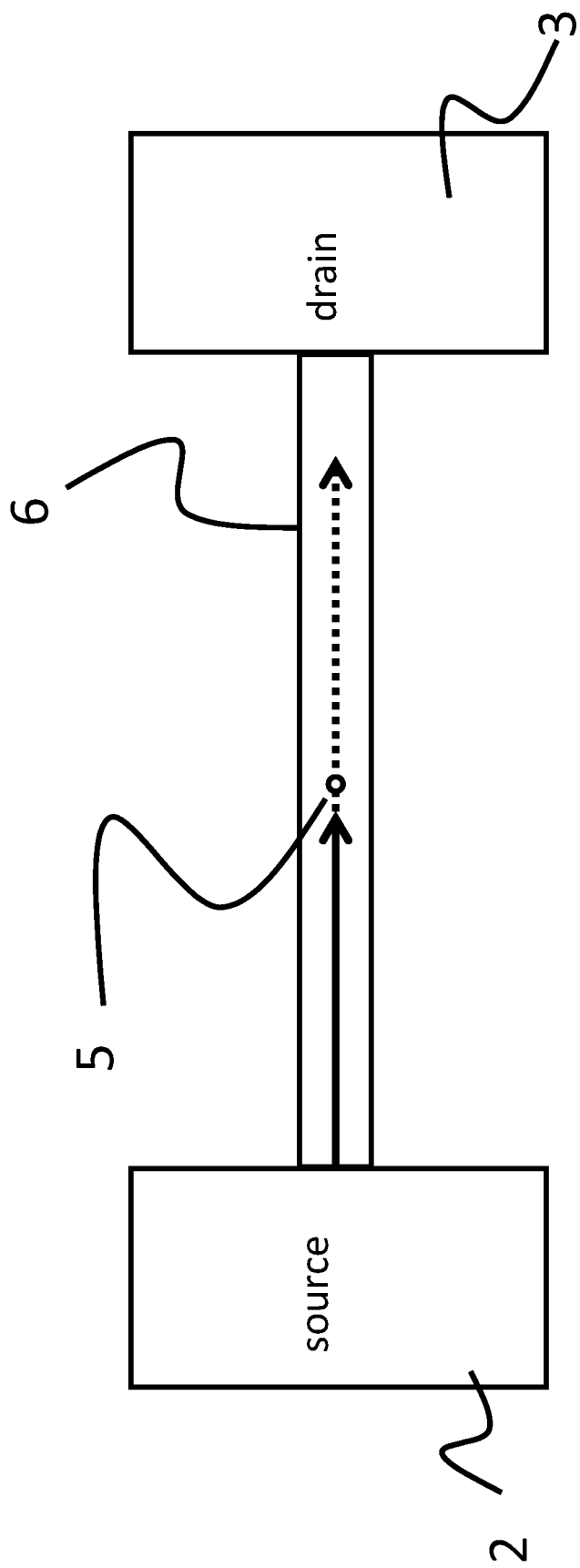
FIG. 7 is a view illustrating that electrons cannot flow around the charge in the prior art biosensor.

In FIG. 9, there are three conducting wires 6, each of which can detect a sole composite body 5 on the surface of the oxide film 1. The sense-amplifiers 9 corresponding to those conducting wires 6 can detect the reduction of a current signal thanks to charges of those composite bodies 5. The difference between the embodiment of the semiconductor biosensor related to the present invention and the conventional semiconductor biosensor shown in FIG. 5 is that the common drain 3 was replaced with a plurality of the sense-amplifiers 9 each of which is connected to one of the conducting wires 6 independently. By such arrangement, it is theoretically made possible to distinguish a change in electric current from one of the conducting wires 6 attributable to a sole composite body 5, by not adding signals from every conducting wire 6 up.

Next, the method for distinguishing a signal from noise is described. There are M conducting wires 6 and M sense-amplifiers 9. The M sense-amplifiers 9 and the common source 2 are connected at the opposite side of the M conducting wires 6 as shown in FIG. 9. It is supposed that m conducting wires 6 of the M ones can detect the sole composite body 5 on the surface of the oxide film 1 in a similar way (In the example of FIG. 9, m=3).

If one conducting wire 6 does not detect any sole composite body 5 on the surface of the oxide film 1, the electric current that flows from the common source 2 to the sense-amplifier 9 that is connected to said one conducting wire 6 is denoted as $I_0$. On the other hand, if one conducting wire 6 detects a sole composite body 5 on the surface of the oxide film 1, the electric current that flows from the common source 2 to the sense-amplifier 9 that is connected to said one conducting wire 6 is denoted as $I_1$. The electric current $I_1$ can be expressed as the sum of electric current $I_0$ and a difference $\Delta I$ between currents $I_0$ and $I_1$. Namely, $I_1 = I_0 + \Delta I$. In this regard, if the conventional semiconductor biosensor is used for inspection, the common drain 3 will receive an electric current from each conducting wire 6 that has a magnitude of $I_0 + (m/M) \times \Delta I$ on average. On the other hand, the sense-amplifier 9 of the biosensor in this embodiment, that is connected to the conducting wire 6 detecting the sole composite body 5 on the surface of the oxide film 1, is able to receive the electric current of $I_0 + \Delta I$. In other words, the sense-amplifier 9 in the embodiment is able to determine whether the conducting wire 6 detects the sole composite body 5 based on the electric current of $I_0 + \Delta I$. In contrast, the common drain 3 of the conventional biosensor can only determine whether a single conducting wire 6 detects the sole composite body 5 based on the electric current of $I_0+(m/M)\times\Delta I$. The sense-amplifier 9 of the application receives an extra amount of current of $\Delta I\times(1-m/M)$ in addition to the average current received by the conventional common drain 3. As such, the value of $(1-m/M)$ can serve as a standard for evaluating the level of improvement to the Limit of Detection (LOD) in the embodiment.

The improving factor of LOD is given by Formula 3.

$$\varepsilon \cong 1 - \frac{m}{M} \quad \text{[Formula 3]}$$

An accidental current change on the conducting wires 6 is noise, misleading the conducting wires 6 without the composite body 5 to be considered as having one. Assuming the number of the conducting wires 6 with noise is δ, the noise is made ignorable as long as m is large enough compared with δ. The total number of conducting wires 6 (M) should be made larger, in order to enlarge m while not degrading the limit of detection. Thereby, the improved LOD by the present invention, Formula 4, is obtained.

$$\text{Improved } LOD = (1 - \varepsilon) \times LOD = \frac{m}{M} \times LOD \quad \text{[Formula 4]}$$

In the example where the gate width of the biosensor (i.e., the width of central reaction unit 200) is 2.4 mm, where the width of the conducting wire is 3 nm on average, and where the space between the adjoining conducting wires 6 is 57 nm on average, there are 40,000 conducting wires 6. When the improving factor ε (Formula 3) is 99.9%, m is 40. Indeed, there may be conducting wires 6 in which the electric current is accidentally decreased. Namely, the possibility of the presence of the conducting wires 6 with noise is non-zero. However, the number of those conducting wires (δ) may be less than 40. When the improving factor is 99%, m is 400 which may be larger than δ. When the improving factor is 90%, m is 4000, which may be much larger than δ. Even for a 90% improving factor, the improving ratio (m/M) may be large enough.

The total number of the conducting wires 6 (M) is predetermined in the step of a device design, which will be described below with an example of a fabrication method of the central reaction unit 200.

Figure 11:
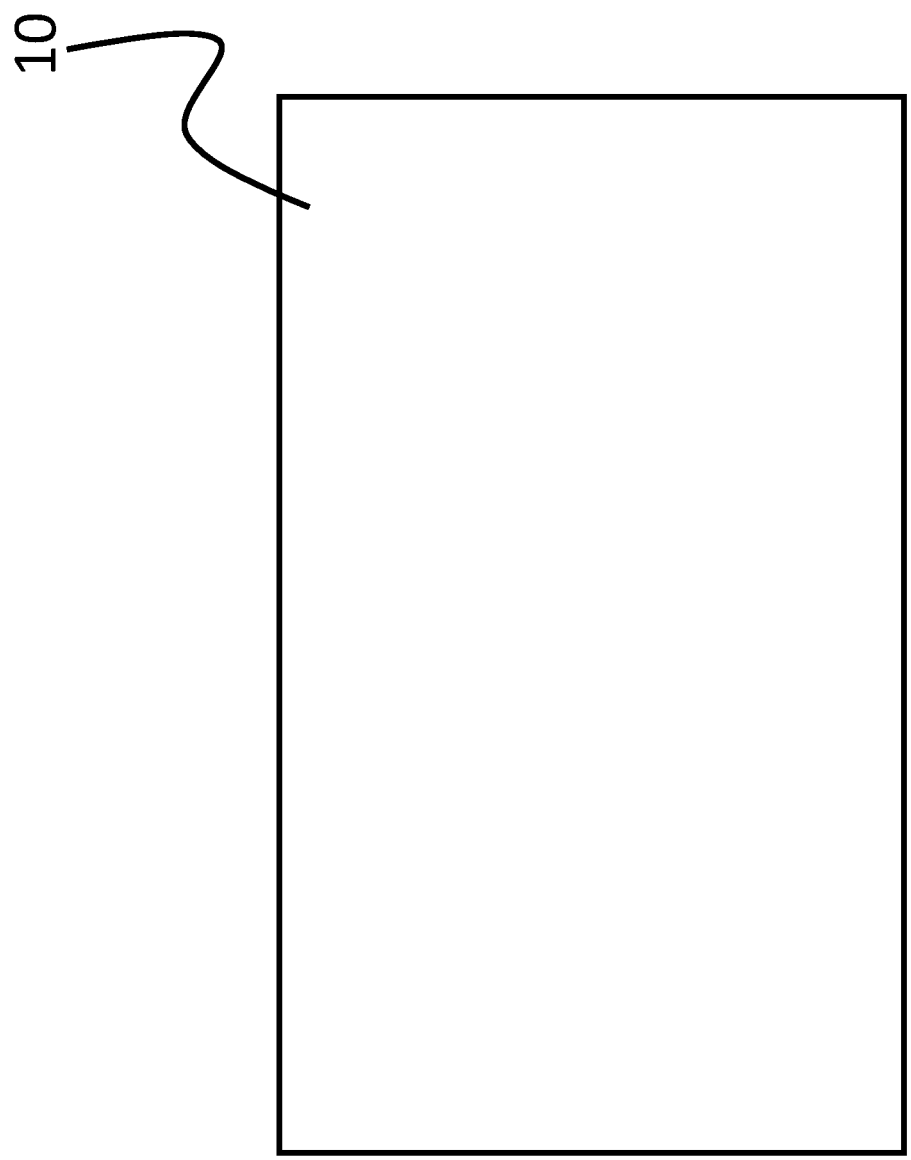
FIG. 11 is a view illustrating a fabrication method of a biosensor related to an embodiment of the present invention.
Figure 12:
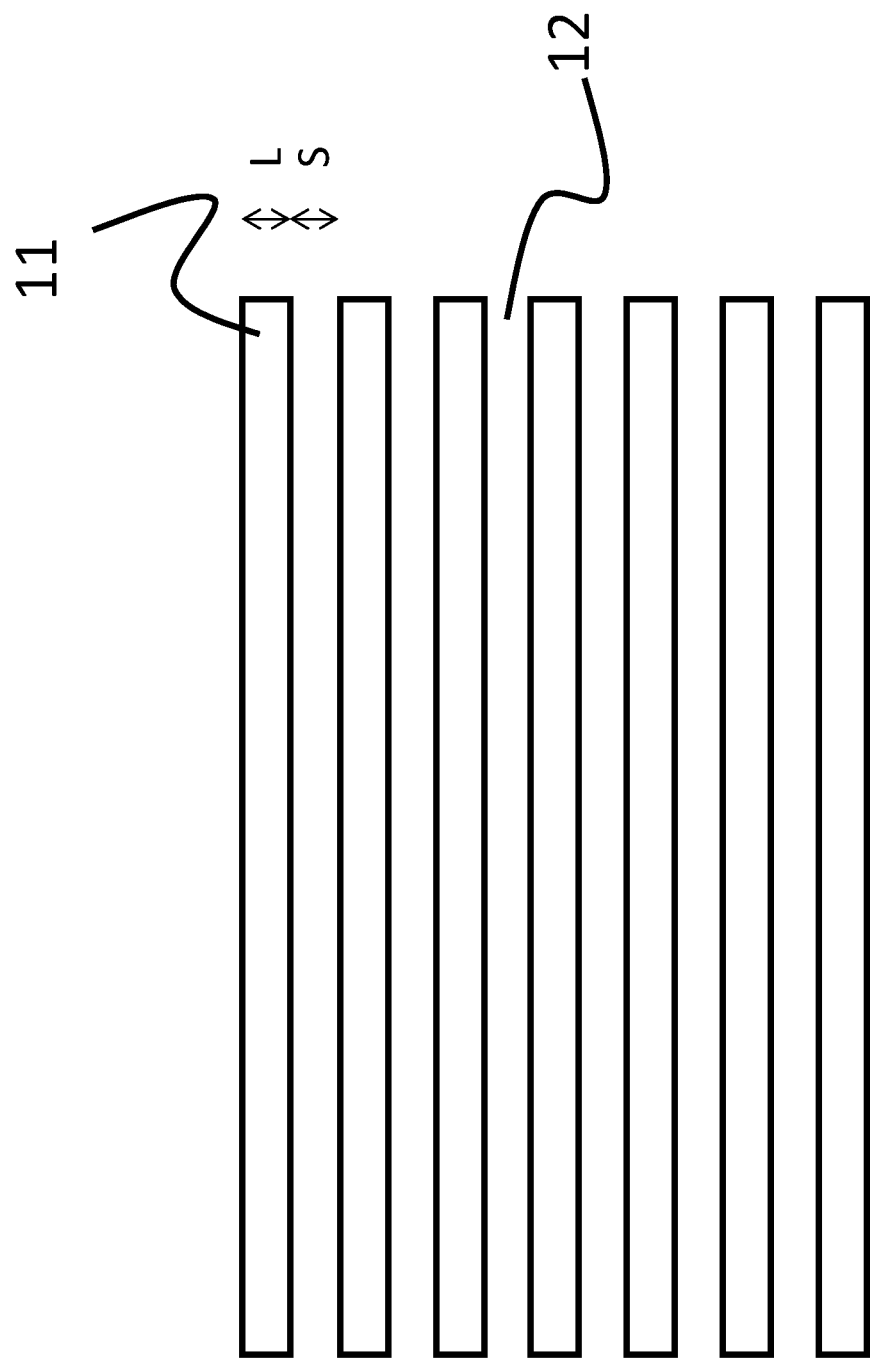
FIG. 12 is a view illustrating a fabrication method of a biosensor related to an embodiment of the present invention.

In FIG. 11, there is a SOI (Silicon-On-Insulator) film 10 with the thickness being 20 nm as an example. This SOI film 10 is cut out to the line 11 and the space 12 in the lithography process, as illustrated in FIG. 12. The width of the line 11 (L) and the width of the space 12 (S) are 30 nm. The lines 11 correspond to semiconductor wires. By this way, a plurality of the semiconductor wires 11 with cross-sections being (30 nm, 30 nm, 20 nm) on average are made.

Next, an oxide film is compensated to the spaces 12, and, then, the semiconductor wires 11 are slimmed by subsequent thermal processes (sliming process).

Figure 13:
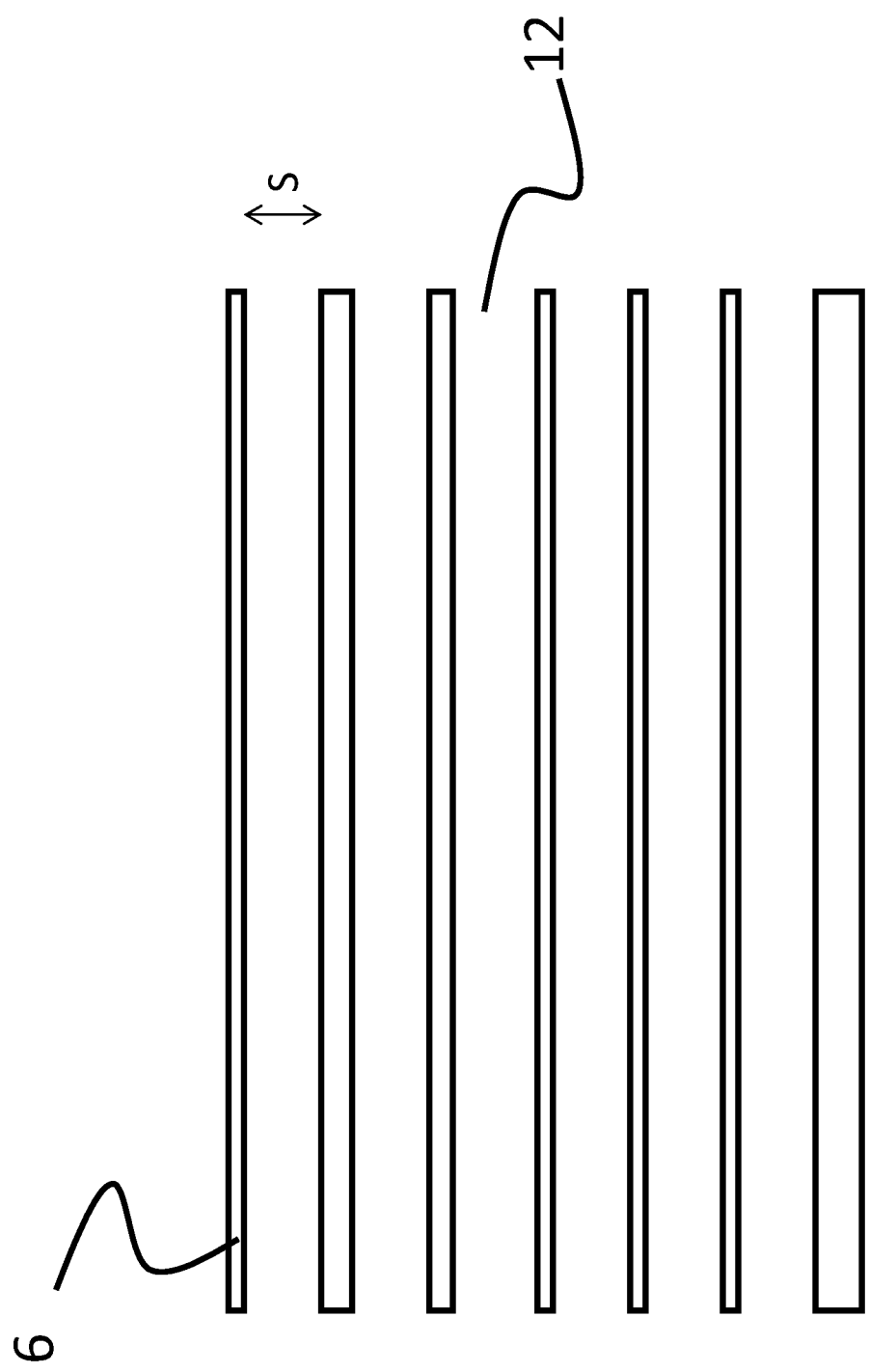
FIG. 13 is a view illustrating a fabrication method of a biosensor related to an embodiment of the present invention.

As a result, the conducting wires 6 with a diameter being 3 nm on average and the spaces 12 with a width being 57 nm on average are arranged, as illustrated in FIG. 13. Subsequently, a CMP (Chemical and Mechanical Process) and oxidization are preceded. A thin oxide film 1 is formed after planarization to perform as a gate oxide. Furthermore, the receptors 8 are fixed on the surface of the oxide film 1, and the central reaction unit 200 is made in FIG. 8.

Figure 14:
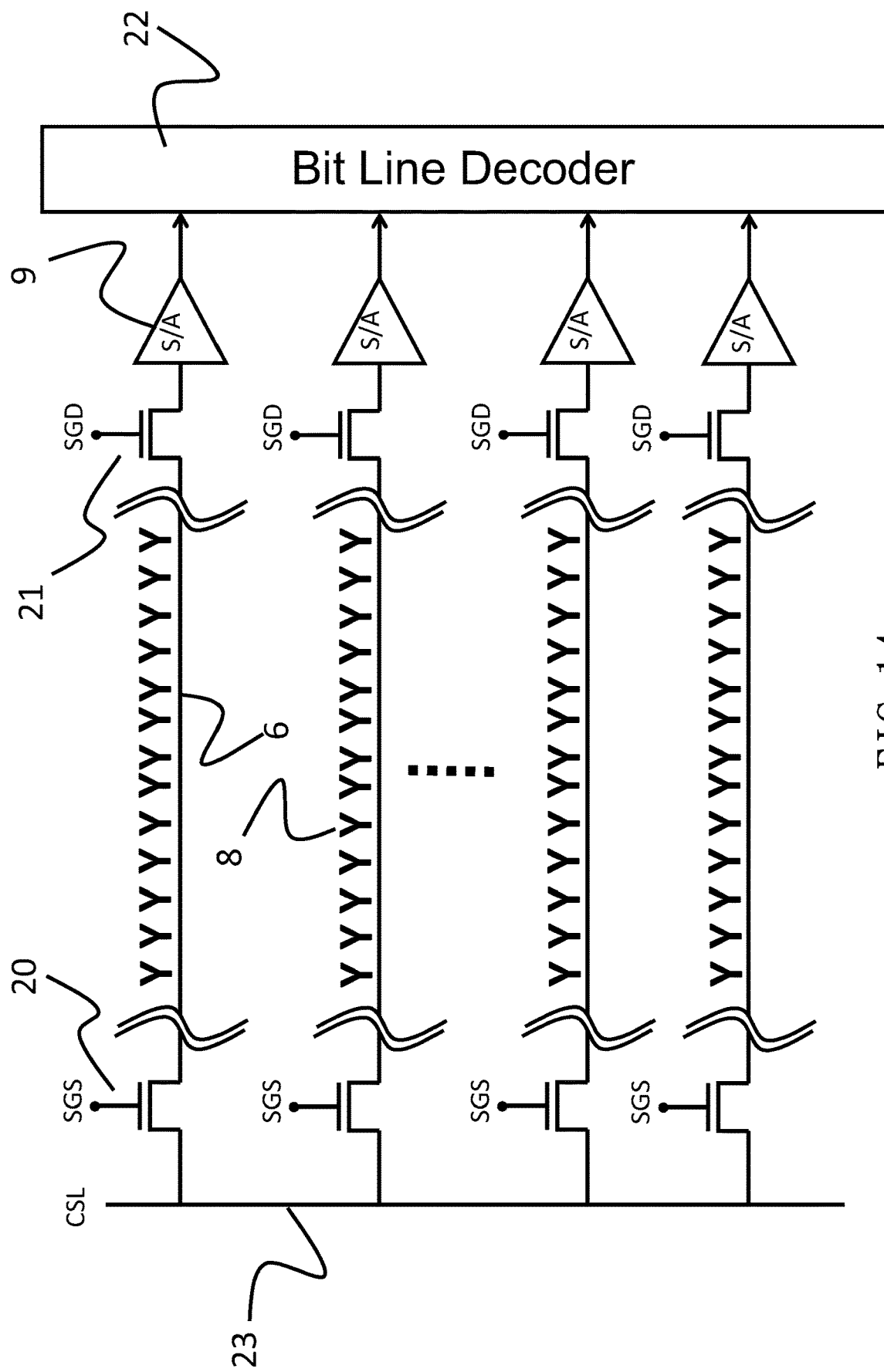
FIG. 14 is a view illustrating an equivalent circuit related to an embodiment of the present invention.

FIG. 14 illustrates an equivalent circuit of the embodiment of the semiconductor biosensor related to the present invention. An end of the conducting wire 6 is connected to a common source line (CSL) via a source select gate 20 (SGS). The other end is connected to the sense-amplifier 9 via a drain select gate 21 (SGD). The signal from each sense-amplifier 9 is analyzed by a bit line decoder 22.

Figure 15:
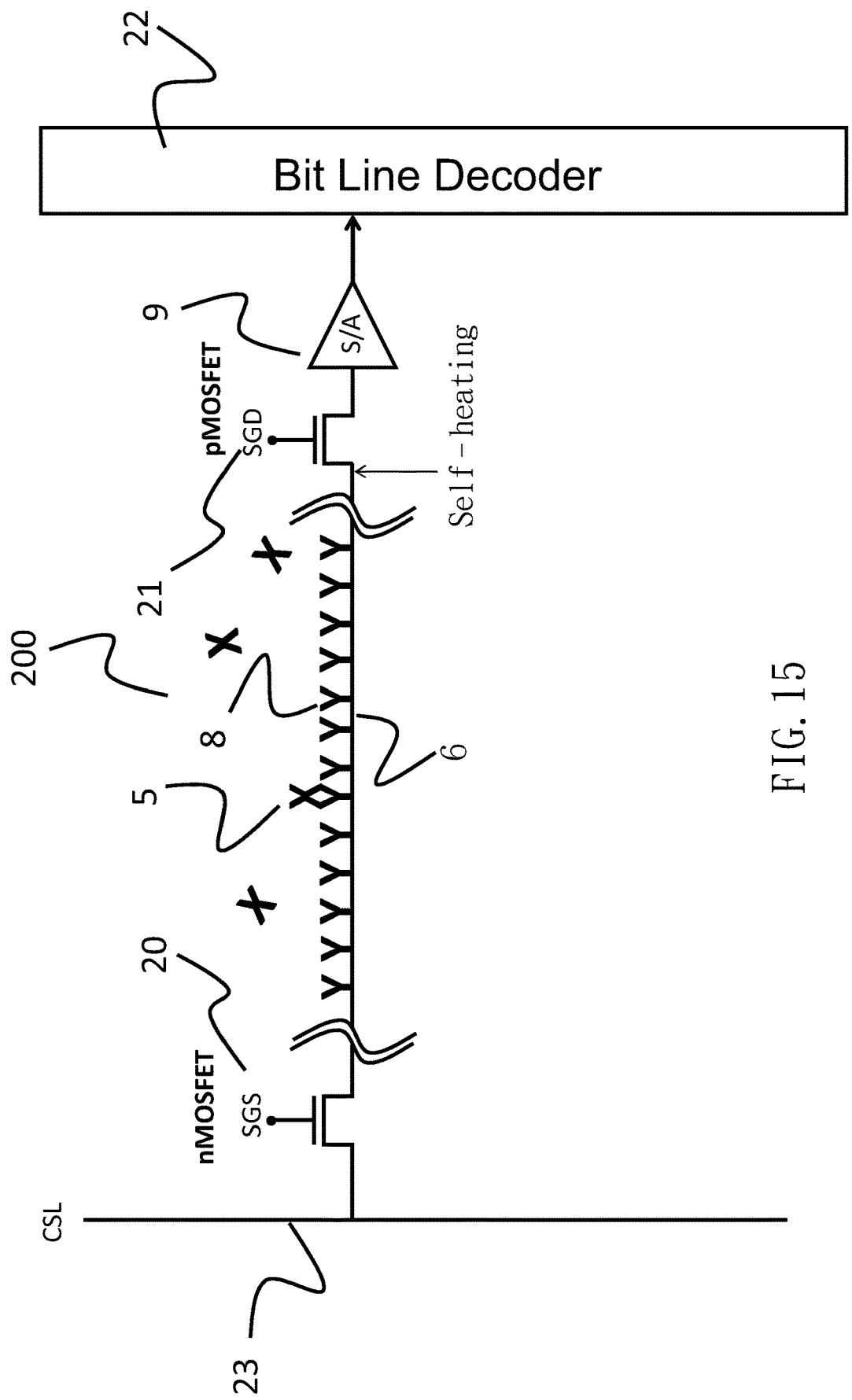
FIG. 15 is a view illustrating that those receptors catch targets in the equivalent circuit of the biosensor related to an embodiment of the present invention.

FIG. 15 is an illustration obtained by picking up a sole conducting wire 6 from the equivalent circuit and hiding the others in FIG. 14. This is for paying attention to the operation of the conducting wire 6 related to the present invention. As an example, the source select gate 20 is an nMOSFET, and the drain select gate 21 is a pMOSFET. In general, the four combinations of SGS 20 and SGD 21 are possible; for example, (nMOSFET and nMOSFET), (nMOSFET and pMOSFET), (pMOSFET and nMOSFET), and (pMOSFET and pMOSFET).

While both of the source select gate 20 and the drain select gate 21 are turned on, electron current flows from an n-type diffusion layer of the source select gate 20 to the conducting wire 6 by applying a drain voltage via the sense-amplifier 9. It is noted that the conducting wires 6 generally exhibit a low thermal conductivity if the diameter is very small, so the heating dissipation is difficult for the conducting wires 6, which leads to a self-heating effect. Thus, in order to cool the conducting wires 6 down, it is preferable to dissipate the heat to a p-type diffusion layer of the drain select gate 21 if the diameter is very small. Therefore, the drain select gate 21 can be a pMOSFET.

The electric current flowing through the conducting wire 6 is made of electrons flowing therein. If the charge stored by the composite bodies 5 is negative, the signal sensed by the sense-amplifier 9 is reduced by the charge. Otherwise, the signal is increased by the charge.

Figure 16:
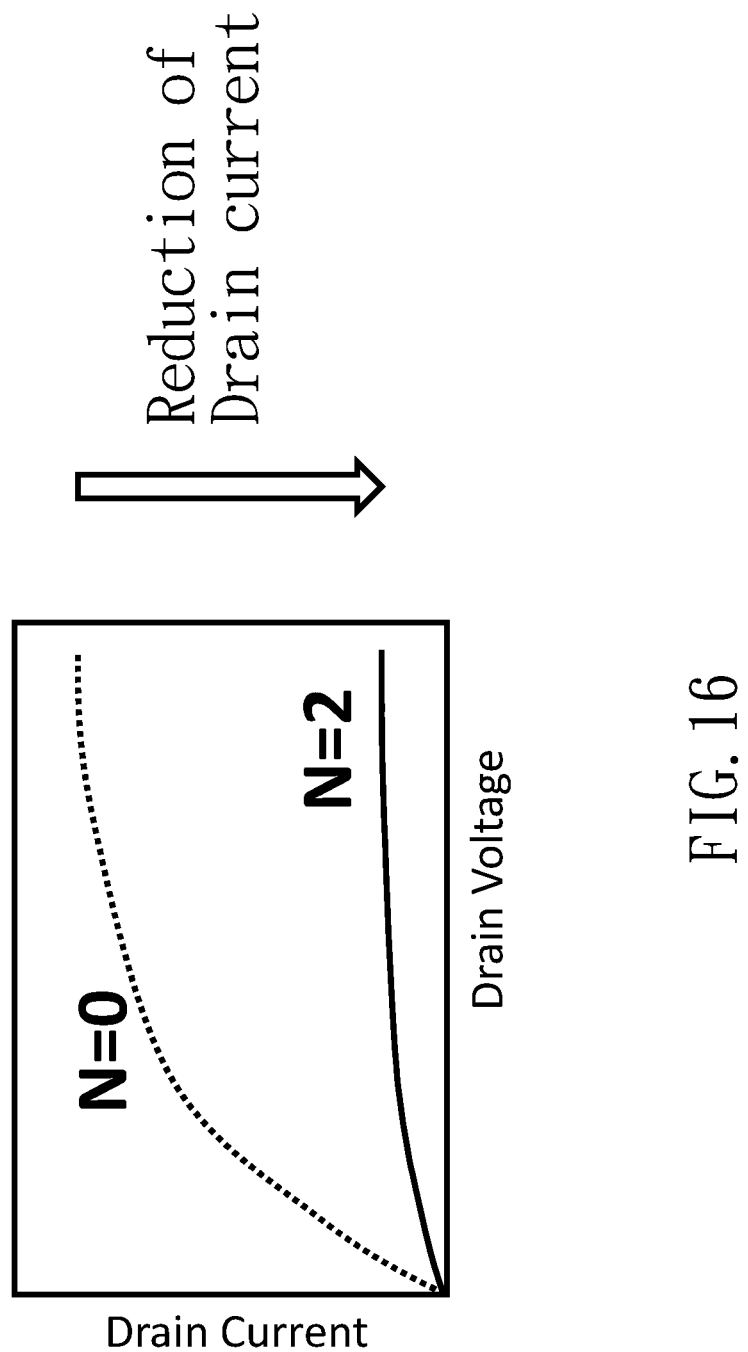
FIG. 16 is a view illustrating that a signal electric current is modulated with regard to a charge carried by those targets in the biosensor related to an embodiment of the present invention.

FIG. 16 is an illustration of the drain current (current sensed by the sense-amplifiers 9) with no composite body 5 attached on the conducting wire 6 (N=0) and with the composite bodies 5 having two electrons attached on the conducting wire 6 (N=2). To sense the difference in current is to detect the existence of the target 7.

Figure 17:
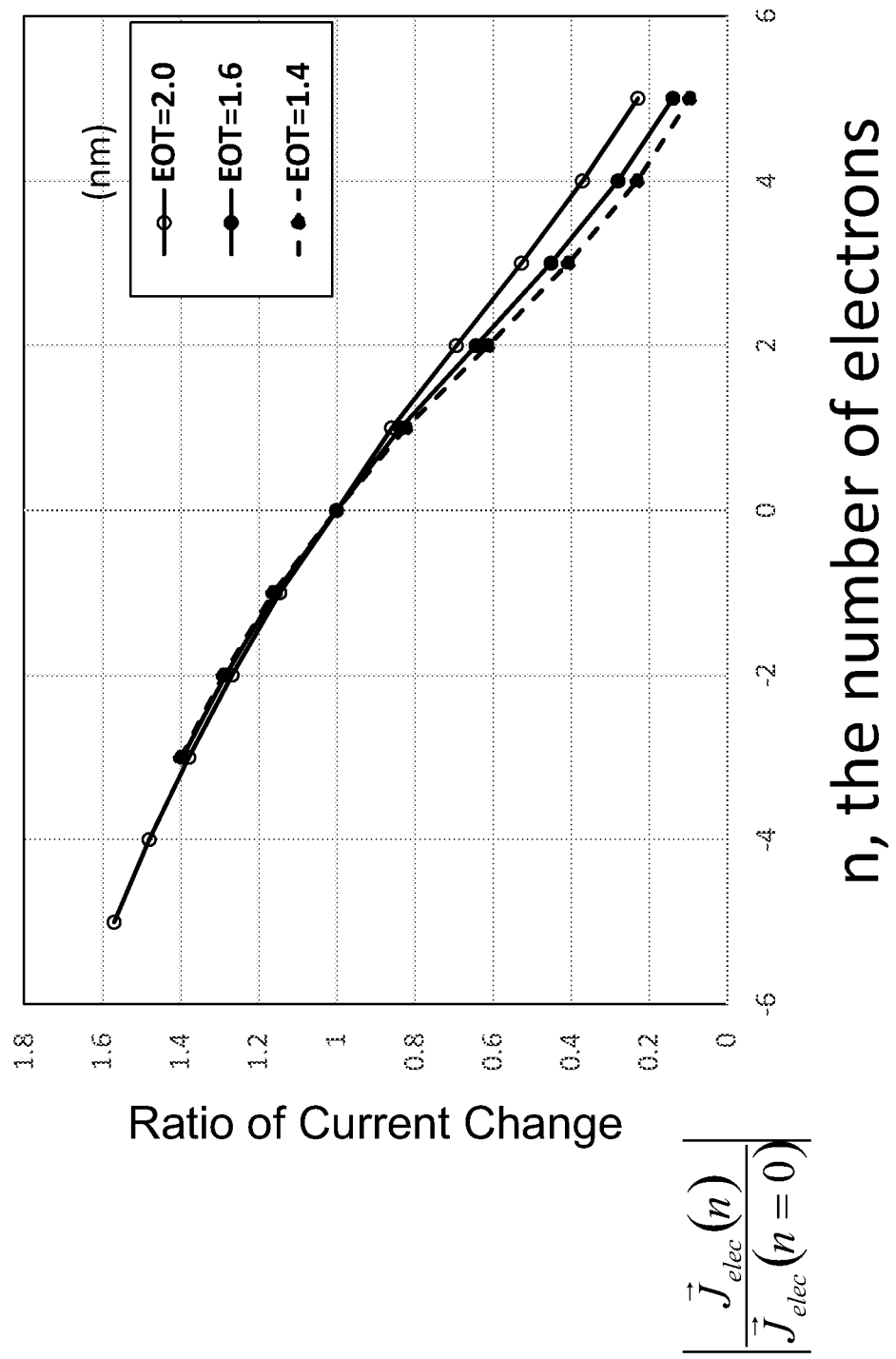
FIG. 17 is a view illustrating a simulation result of the operation of the biosensor related to an embodiment of the present invention.

The result of a device simulation with a different amount of composite bodies 5 attached to the conducting wire 6 is shown in FIG. 17. The ratio of the current to that with no composite body 5, which is neutral (N=0), is plotted with respect to the number of electrons (n) stored in the composite body 5. As the number of electrons increases, the ratio of the current is reduced to about half at n=3, or about 20% at n=4. It is able to detect the current change with this level of reduction with a standard sense-amplifier.

The EOT is the Equivalent Oxide Thickness of some dielectric films between the target 7 and the conducting wire 6, to which the thickness of the dielectric film is converted. The sensitivity is improved as EOT is decreased. It is preferable that EOT is less than 2 nm from this simulation result.

As illustrated in FIG. 13, the production tolerance is not negligible in actual fabricated line-and-space structures. The resistivity of the conducting wire 6 is increased as the diameter of the conducting wire 6 becomes smaller, and is decreased as it becomes larger. This fluctuation of the diameter of the conducting wire 6 induces the noise contaminated into signals sensed by the sense-amplifiers 9.

Figure 18:
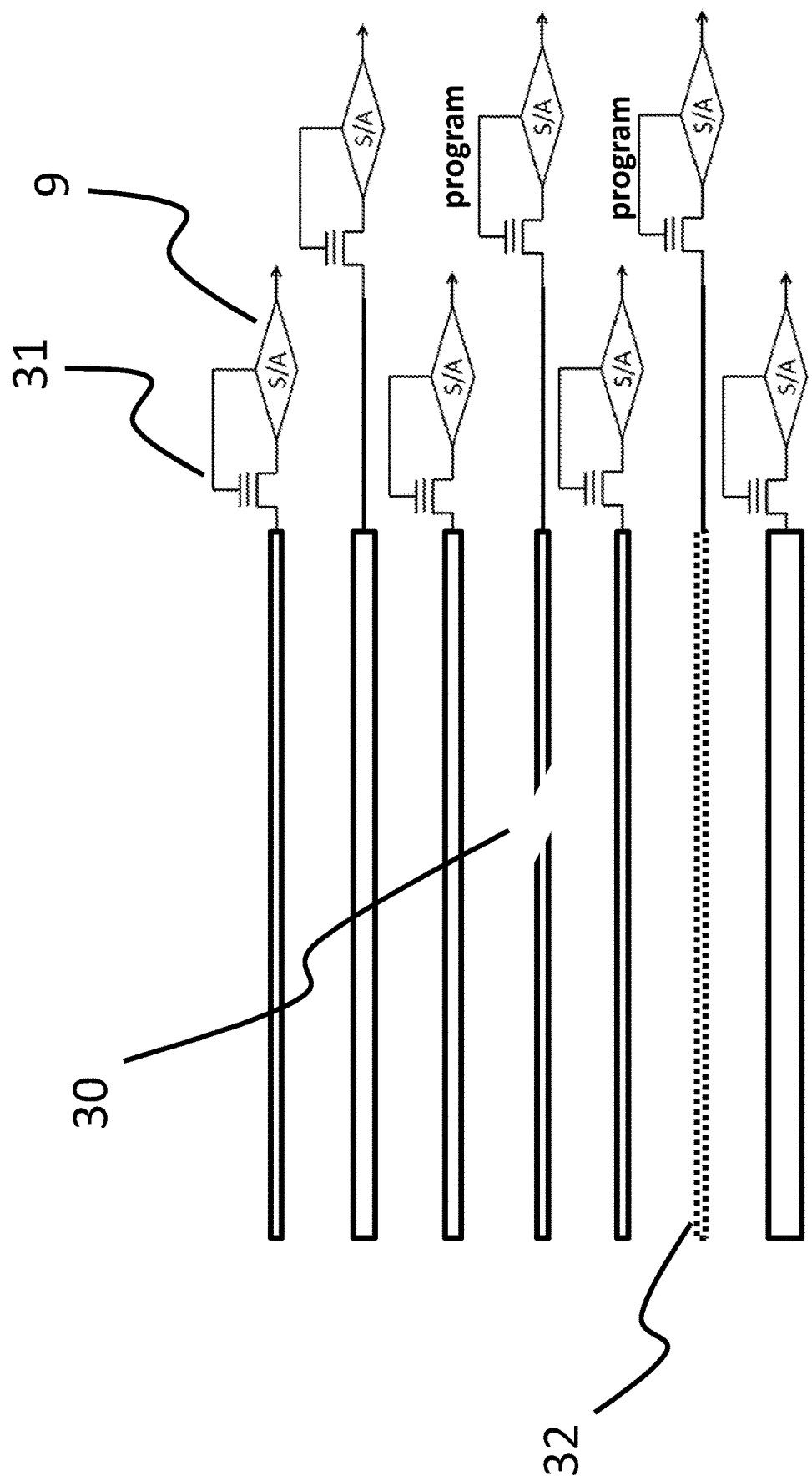
FIG. 18 is a view illustrating a method for correcting the error modes of the biosensor related to an embodiment of the present invention.
Figure 19:
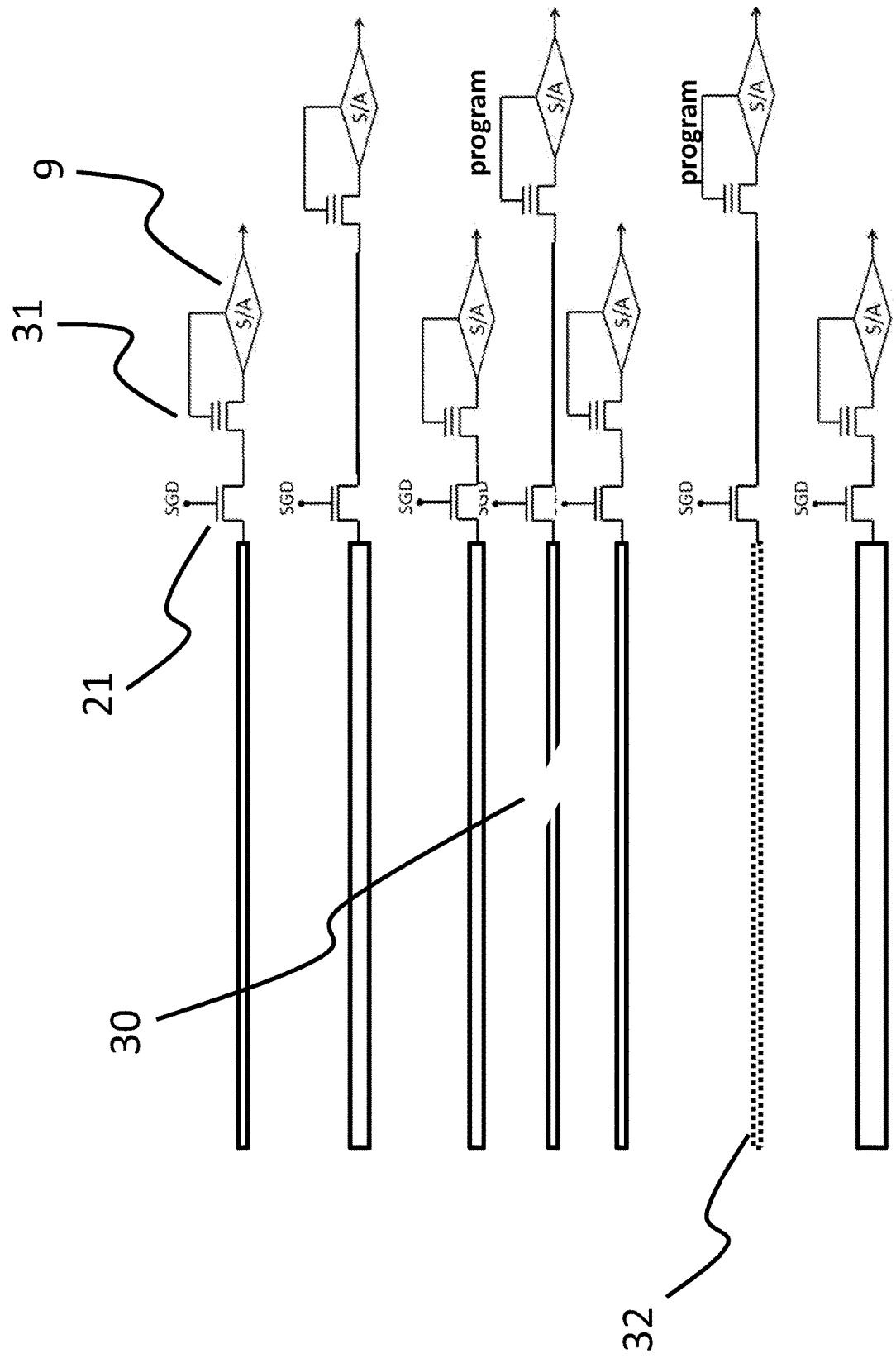
FIG. 19 is a view illustrating a method for correcting error modes of the biosensor related to an embodiment of the present invention.

Referring to FIGS. 18 and 19, the resistance of the conducting wires 32 with a diameter being too small is high enough to make the signal undistinguishable from noise. On the other hand, there may also be a snapped conducting wire 30. The snapped conducting wire 30 cannot conduct current, and, thus, the signal from which is also undistinguishable from noise.

FIGS. 18 and 19 illustrate a control method of the semiconductor biosensor related to the present invention for dealing with the production tolerance. In FIG. 18, the drain select gate 21 is replaced with a non-volatile memory type transistor 31. On the other hand, in FIG. 19, the non-volatile memory type transistor 31 is put between the drain select gate 21 and the sense-amplifier 9.

Figure 20:
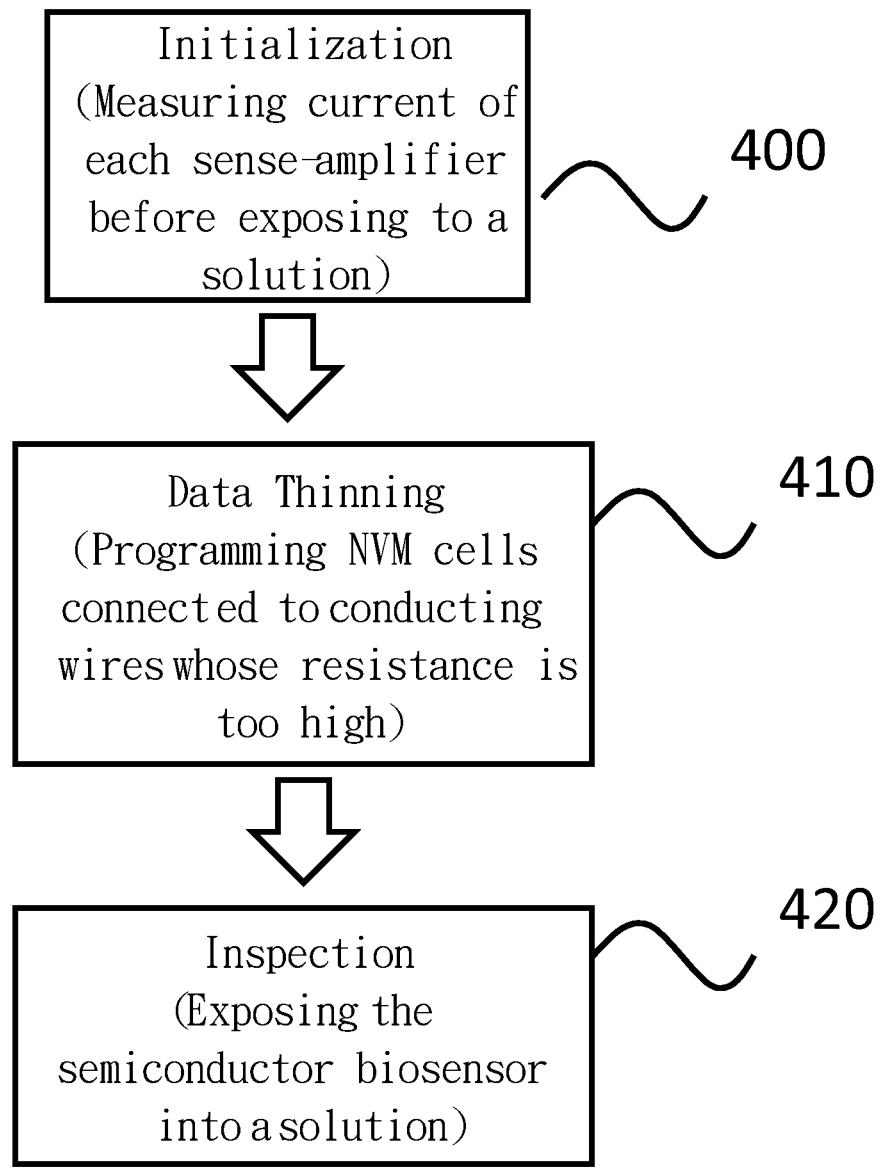
FIG. 20 is a view illustrating a method for correcting error modes of the biosensor related to an embodiment of the present invention.

Firstly, as illustrated in FIG. 20, the electric current is sensed by the sense-amplifier 9 while the central reaction 200 unit is exposed into a solution without the target 7 or is not exposed into any solution. This is the step of Initialization. The conducting wires 6 with no sensible current are regarded as conducting wires 32 with a diameter being too small or as snapped conducting wires 30. Then, the non-volatile memory type transistor 31 related to those conducting wires 6 is programmed. Since the programmed non-volatile memory type transistors 31 are turned off, the data of those conducting wires 6 are not transferred to the sense-amplifier 90. This is the step of Data Thinning. After excluding the conducting wires 32 with a diameter being too small and snapped conducting wires 30, the left-behind conducting wires 6 are utilized for testing by sensing the electric current via the sense-amplifiers 9. This is the step of Inspection.

In general, the operation of the transistor composed of the conducting wire 6 is more influenced by surface states than the conventional MOSFET is. It is because the surface to the volume is larger in the conducting wire 6 than in a substrate constituting the conventional MOSFET. Thereby, more noise is contaminated to the signal through the conducting wire 6 than the signal on the surface of the substrate. The cut-off shown in Formula 2 is determined with respect to the maximum amplitude of the noise.

The amplitude of noise though the conducting wire 6 is sensitive to the diameter of the conducting wire 6. As long as the cut-off is adequate, the amplitude of the noise is less than the limitation of control. Of course, the conducting wires 32 with a diameter being too small or with an anomalously high resistance may induce noise with an amplitude out of the limitation, so the conducting wires 32 with a diameter being too small should be excluded.

It is necessary to take the fluctuation (increase and decrease) in the amplitude of the noise into consideration for adequately determining the cut-off.

Figure 21:
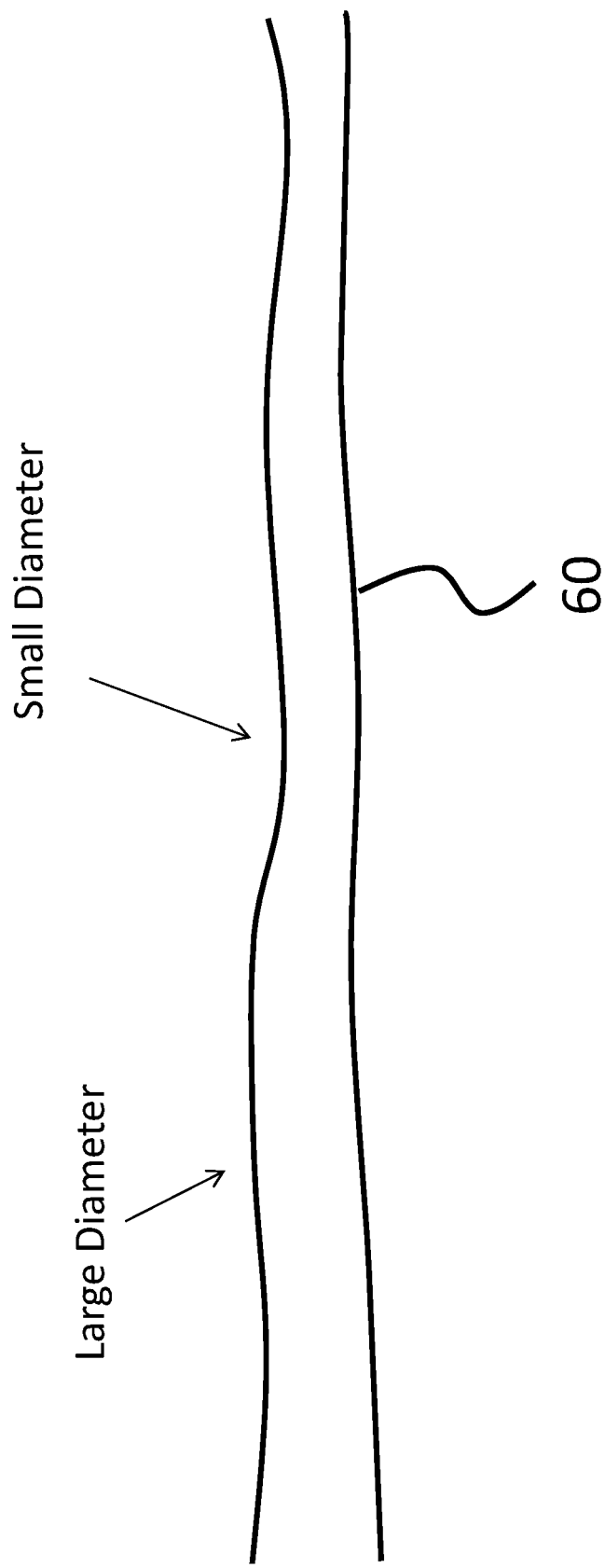
FIG. 21 is a view illustrating fluctuation of a diameter of conducting wires.

In addition, as illustrated in FIG. 21, there is a fluctuation in a diameter even within a sole conducting wire 60, which is a characteristic of the conducting wire 6. It is also necessary to take the fluctuation in the diameter into consideration for adequately determining the cut-off.

Since it is impossible to grasp a fluctuation in the amplitude of the noise or the fluctuation in the diameter when designing the biosensor, it is necessary to tune the cut-off to suppress the impact of those fluctuations.

In concrete, the system with the non-volatile memory type transistor 31, constituting an exemplary embodiment related to the present invention and illustrated in FIGS. 18 and 19, is capable of adequately determining the cut-off.

Figure 22:
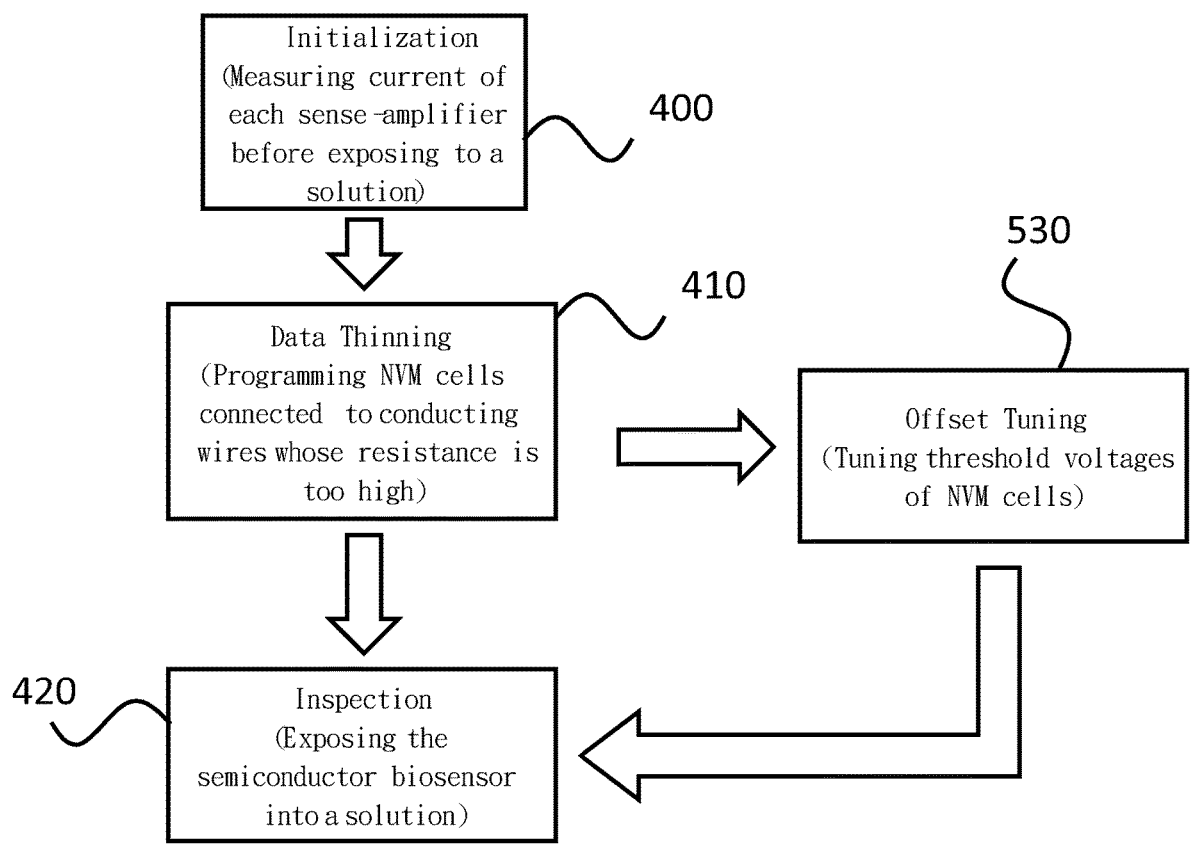
FIG. 22 is a view illustrating a method for correcting an offset of the biosensor related to an embodiment of the present invention.

In another embodiment of the control method of the semiconductor biosensor related to the present invention, as illustrated in FIG. 22, the step of Offset Tuning 530 is appended next to the step of Data Thinning 410 in the flow chart illustrated in FIG. 20. In this step, the resistance of the non-volatile memory type transistor 31 is tuned by arranging the threshold voltage of the non-volatile memory type transistor 31, and thereby, suppressing the impact of the fluctuation in the amplitude of the noise or the diameter.

The method to arrange a threshold voltage of the non-volatile memory type transistor 31 is well-known as verify programming, in which a program-erase is repeated with a small step (short pulse). (See T. Tanaka, et al., 1990 Symposium on VLSI circuits, pp. 105-106 (1990).)

Through the embodiments of the present invention, the limit of detection of the biosensor is substantially improved, which results in the significant enhancement in performance of the semiconductor biosensor and the drastic price reduction of the medical healthcare chip. This enables early detection of disease, which has been impossible with conventional biosensors, and then substantially reduces medical cost.

Figure 23:
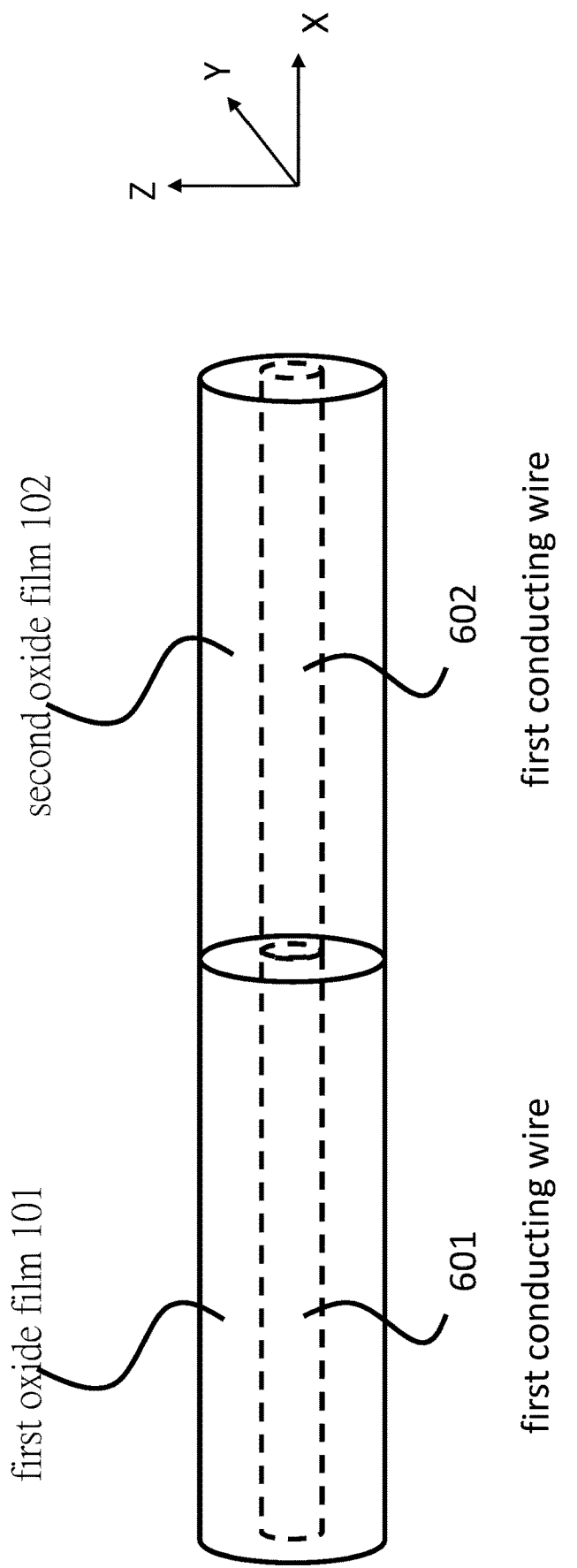
FIG. 23 shows a conducting wire enveloped by an oxide film.
Figure 24:
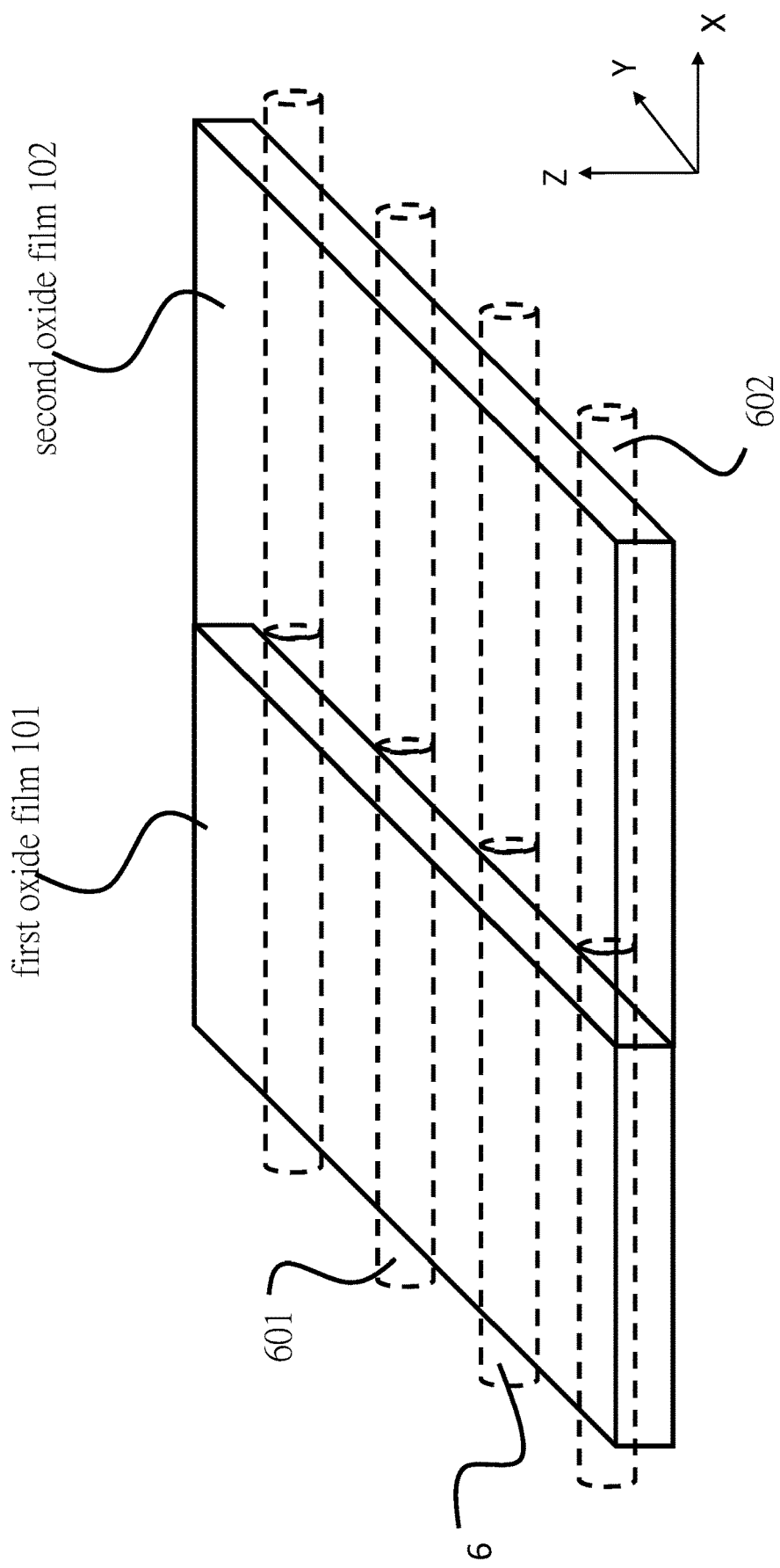
FIG. 24 shows a plurality of conductive wires covered by a first oxide film and a second oxide film.
Figure 25:
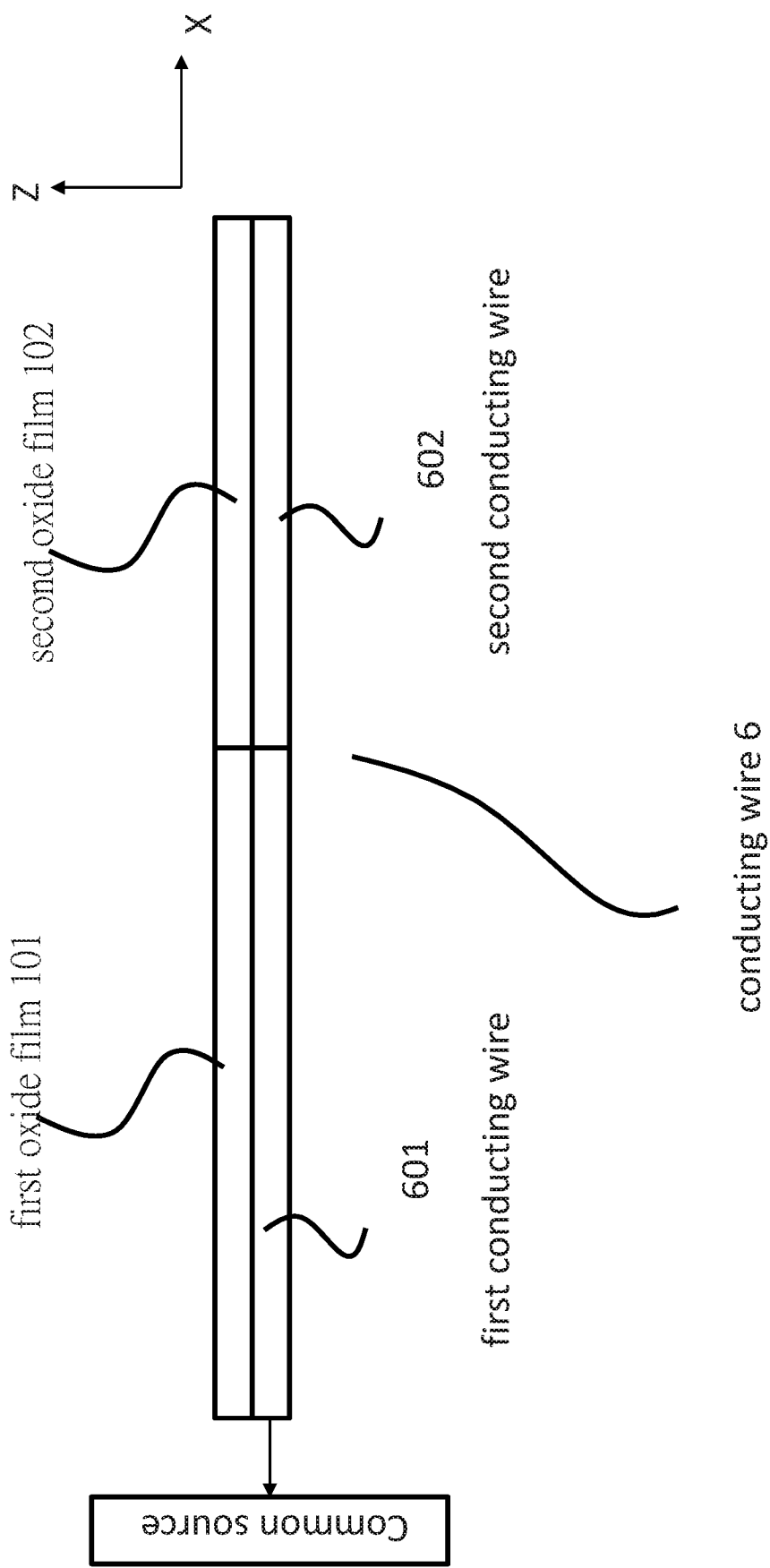
FIG. 25 is a cross sectional view of the system of FIGS. 23 and 24 in a Z-X plane.
Figure 26:
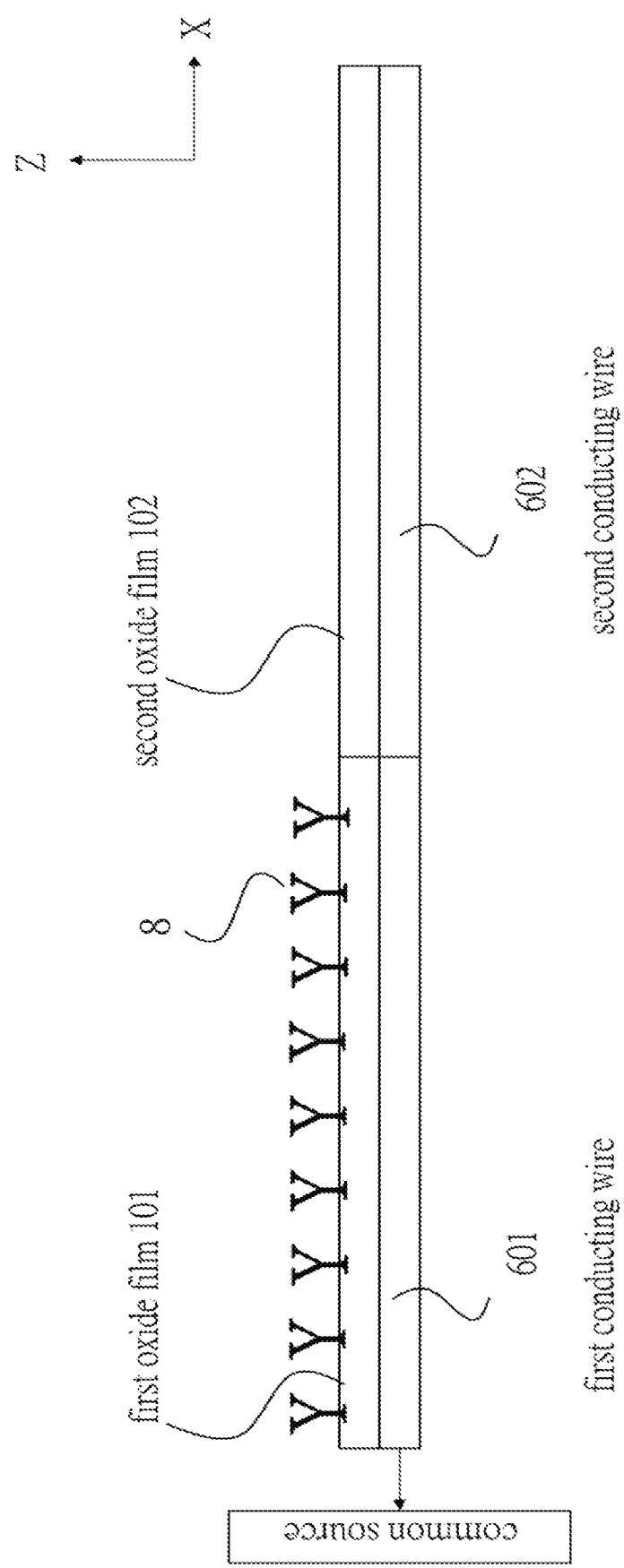
FIG. 26 shows a plurality of receptors 7 on the surface of the first oxide film.
Figure 27:
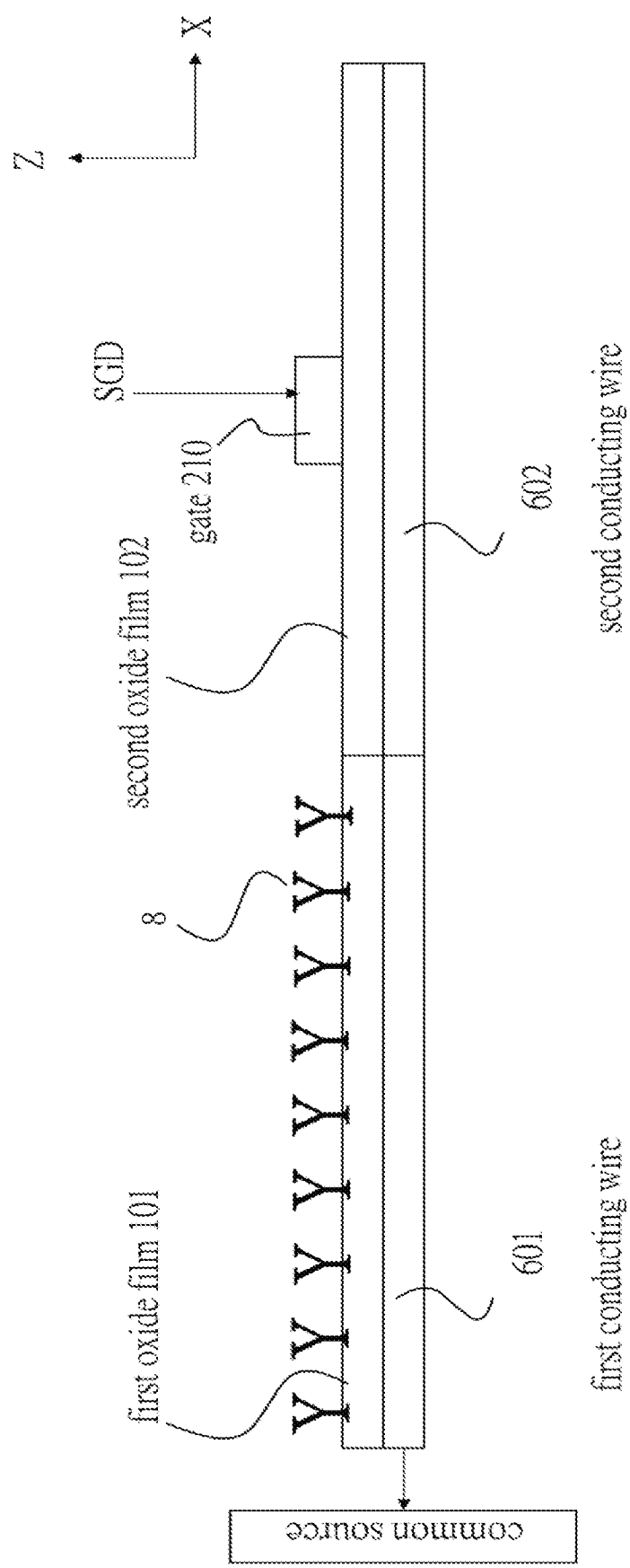
FIG. 27 shows a select gate transistor.
Figure 28:
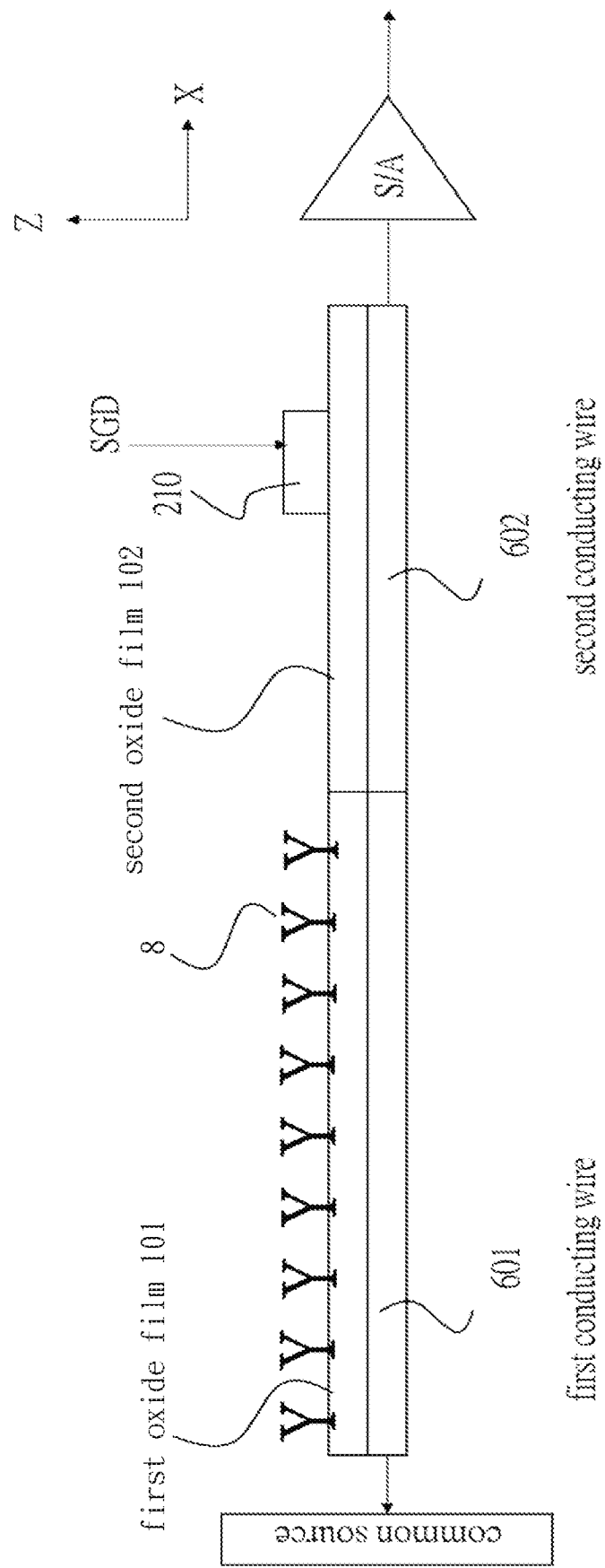
FIG. 28 shows the select gate transistor connected to a sense-amplifier.

FIG. 23 illustrates a conducting wire enveloped by an oxide film. FIG. 24 illustrates a plurality of conductive wires covered by a first oxide film and a second oxide film. FIG. 25 illustrates a cross sectional view of the system of FIGS. 23 and 24 in a Z-X plane. The conducting wire 6 includes a first conducting wire 601 and a second conducting wire 602 connected to the first conducting wire 601. A common source line is connected to an end of the first conducting wire 601 opposite to the second conducting wire 602. The oxide film includes a first oxide film 101 above the first conducting wire 601 and a second oxide film 102 above the second conducting wire 602. In FIG. 26, a plurality of receptors 7 is immobilized on the surface of the first oxide film 101 but not on the surface of the second oxide film 102. In FIG. 27, a transistor includes a gate 210, a part of the second oxide film 102 below said gate 210, and the second conducting wire 602 below the gate 210. If the transistor is used as a select gate transistor, the gate 210 is a select gate. Since this select gate is located at a side opposite to a common source, a sense-amplifier is connected to the second conducting wire 602 at the side opposite to the first conducting wire 601, as is shown in FIG. 28.

Figure 29:
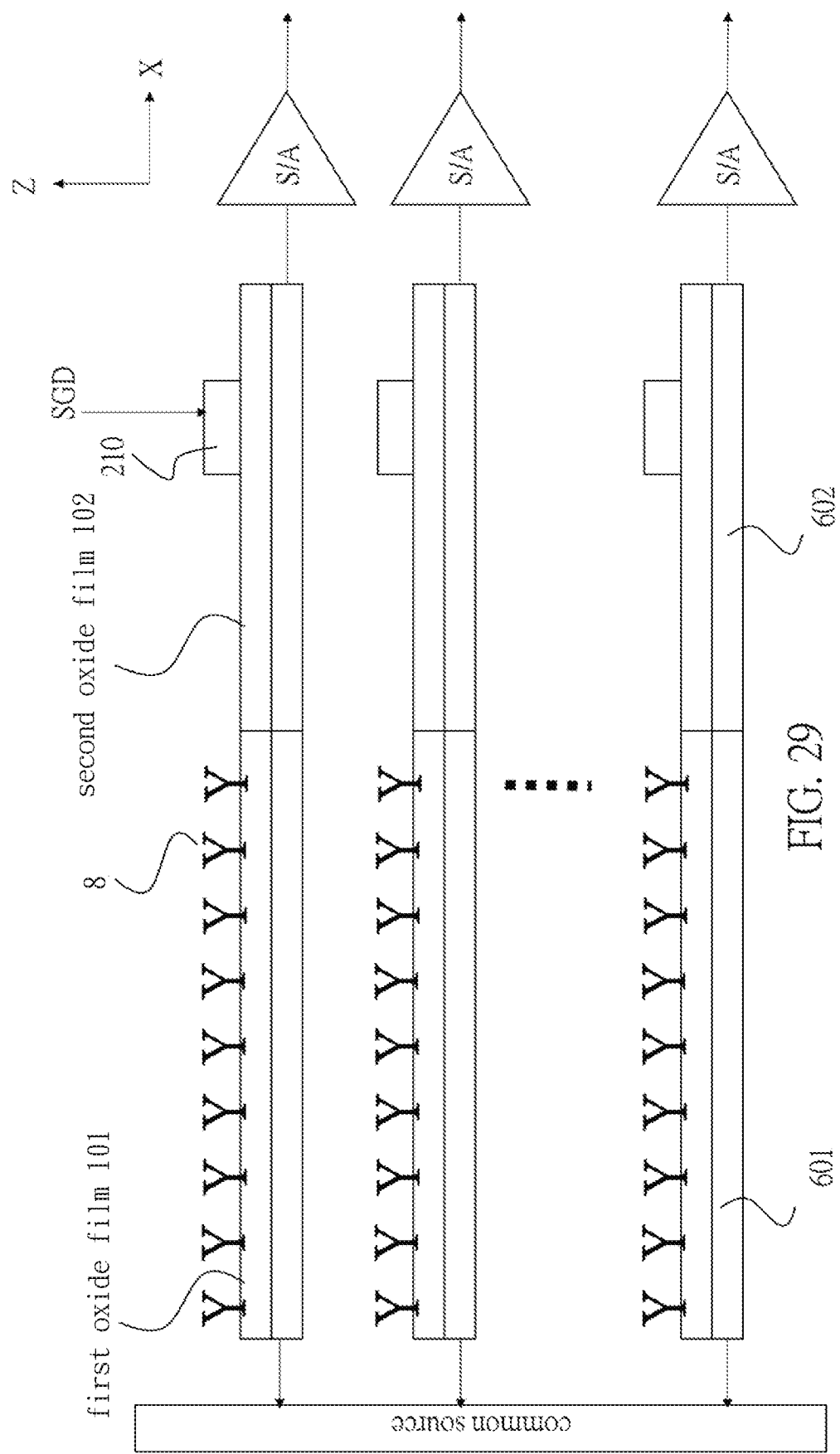
FIG. 29 shows a plurality of select gate transistors connected to a plurality of sense-amplifiers, respectively.

In FIG. 29, there is a plurality of conducting wires 6 including the above-mentioned components (including the drain select gates 210). Note that the plurality of first conducting wires 601 are connected to the common source. On the other hand, the second conducting wires 602 are independently and respectively connected to the plurality of sense-amplifiers.

Figure 30:
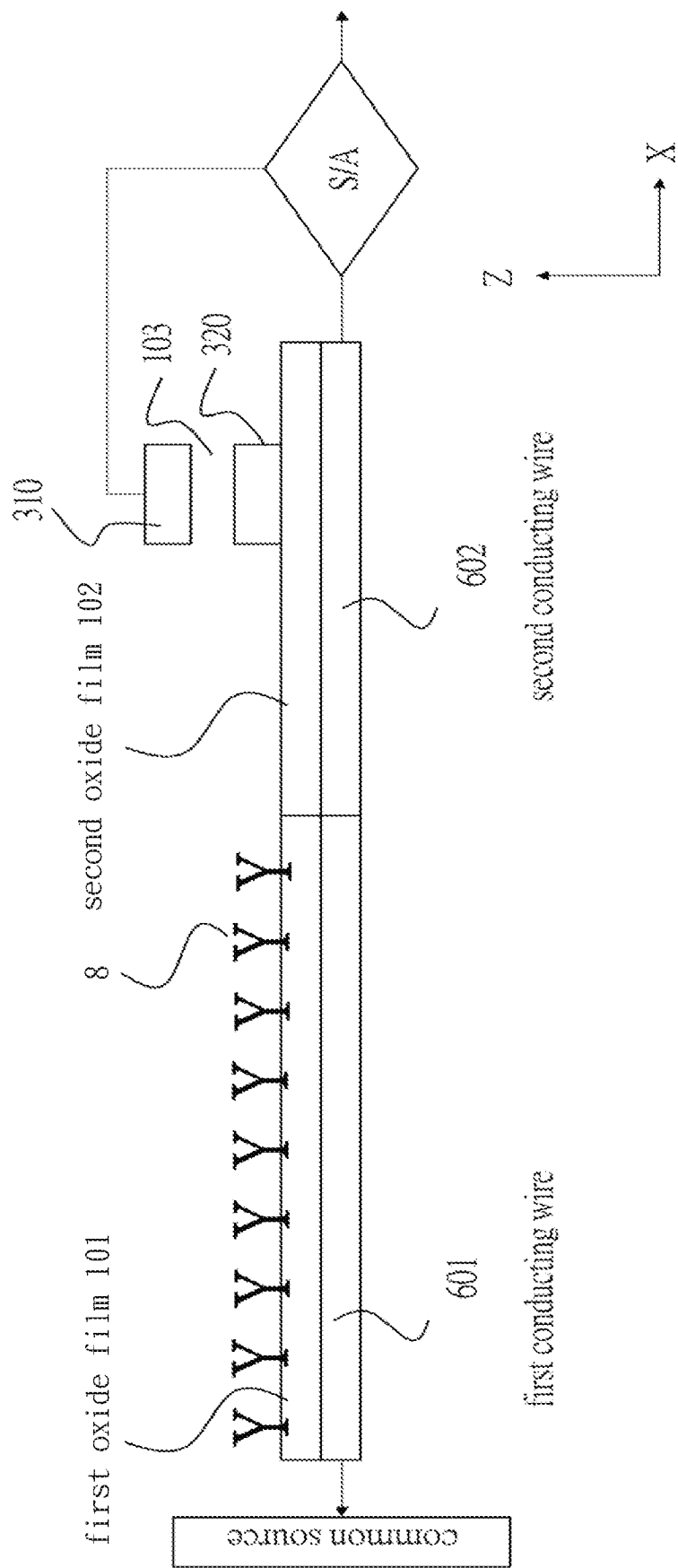
FIG. 30 shows a non-volatile memory type transistor.
Figure 31:
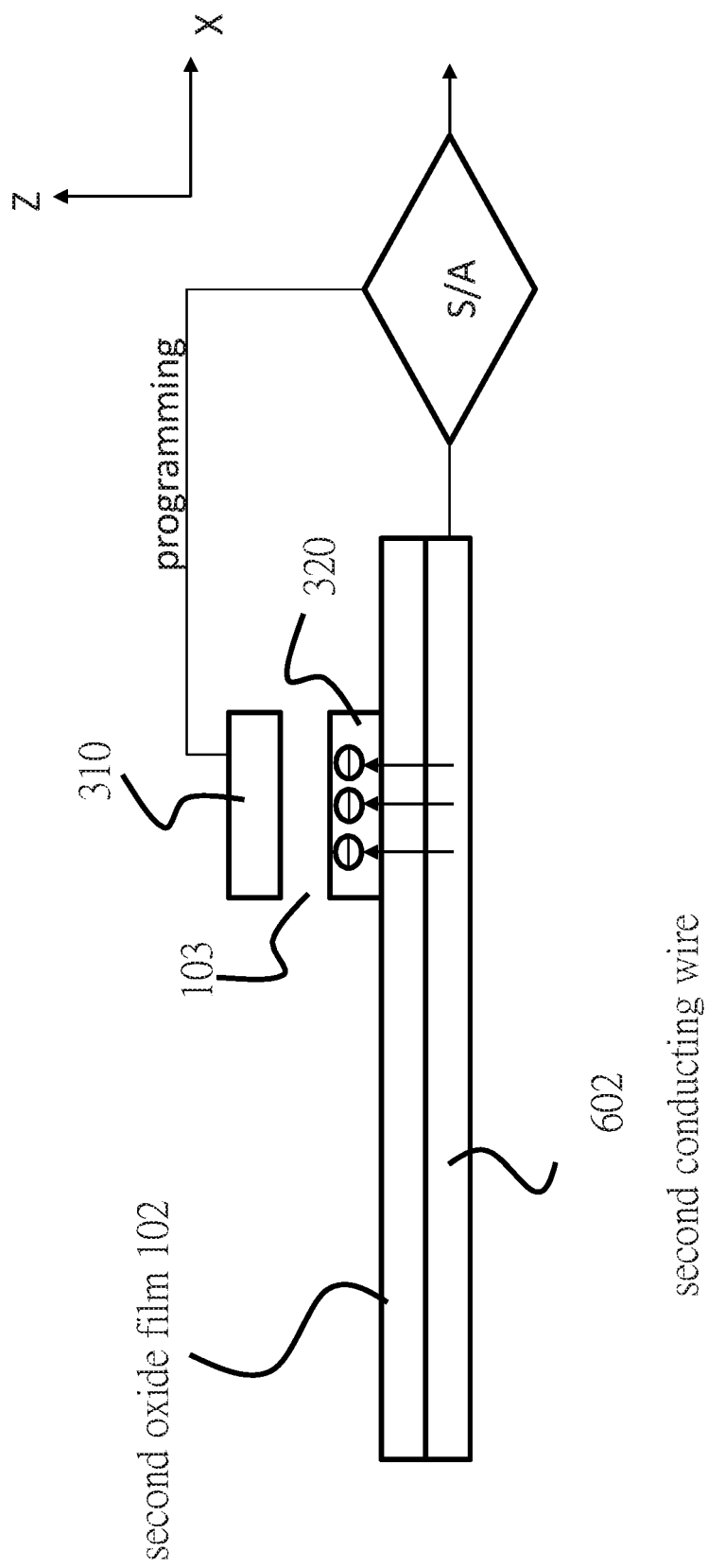
FIG. 31 shows the electrons moving from the second conducting wire to the floating gate.
Figure 32:
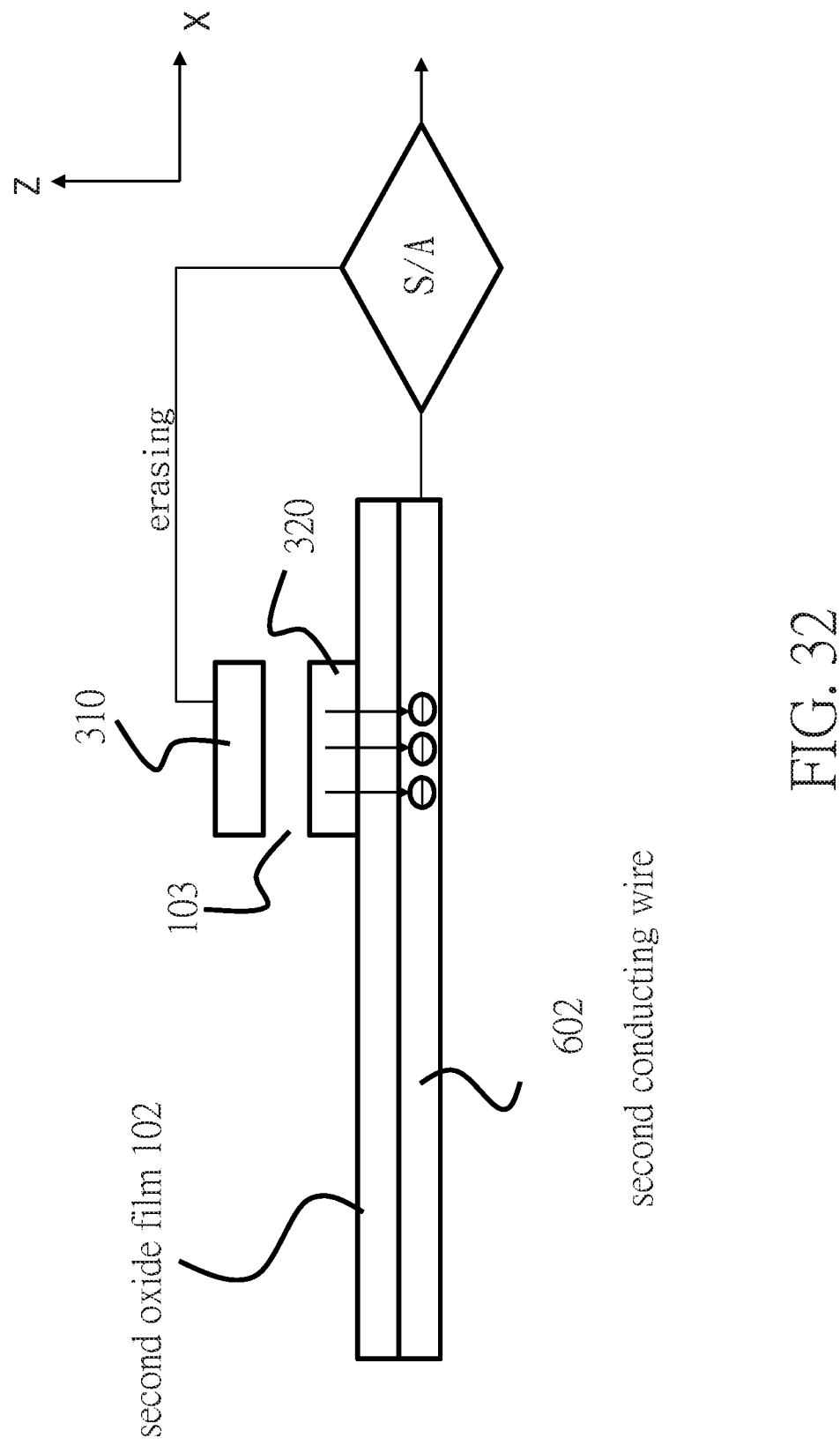
FIG. 32 shows the electrons moving from the floating gate to the second conducting wire.

In FIG. 30, there is a non-volatile memory type transistor including a control gate 310, a third oxide 103, a floating gate 320, a part of the second oxide film 102 below the floating gate 320, and the second conducting wire 602. The control gate 310 is connected to the sense-amplifier also connecting to the second conducting wire 602. The sense-amplifier can sense an output signal of the second conducting wire 602 and then tune a voltage applied on the control gate 310 and the second conducting wire 602 to control the tunneling of electrons between the floating gate 320 and the second conducting wire 602. Note that the sense-amplifier can control a voltage difference between the control gate 310 and the second conducting wire 602 by optimizing a voltage applied to the floating gate 310 and a voltage applied to the second conducting wire 602. If the voltage difference is sufficiently high-positive, the electrons can tunnel from the second conducting wire 602 to the floating gate 320, as illustrated in FIG. 31. This is the programming process. If the voltage difference is sufficiently high-negative, electrons can tunnel from the floating gate 320 to the second conducting wire 602, as illustrated in FIG. 32. This is the erasing process. Said applied voltages can change over time, that is, they are pulses. By this way, the sense-amplifier can tune the charge quantity of the electrons stored in the floating gate 320 by optimizing the duration, amplitude and polarity of the pulses. The threshold voltage of the non-volatile memory type transistor can be controlled by tuning the charge quantity stored in the floating gate 320.

Figure 33:
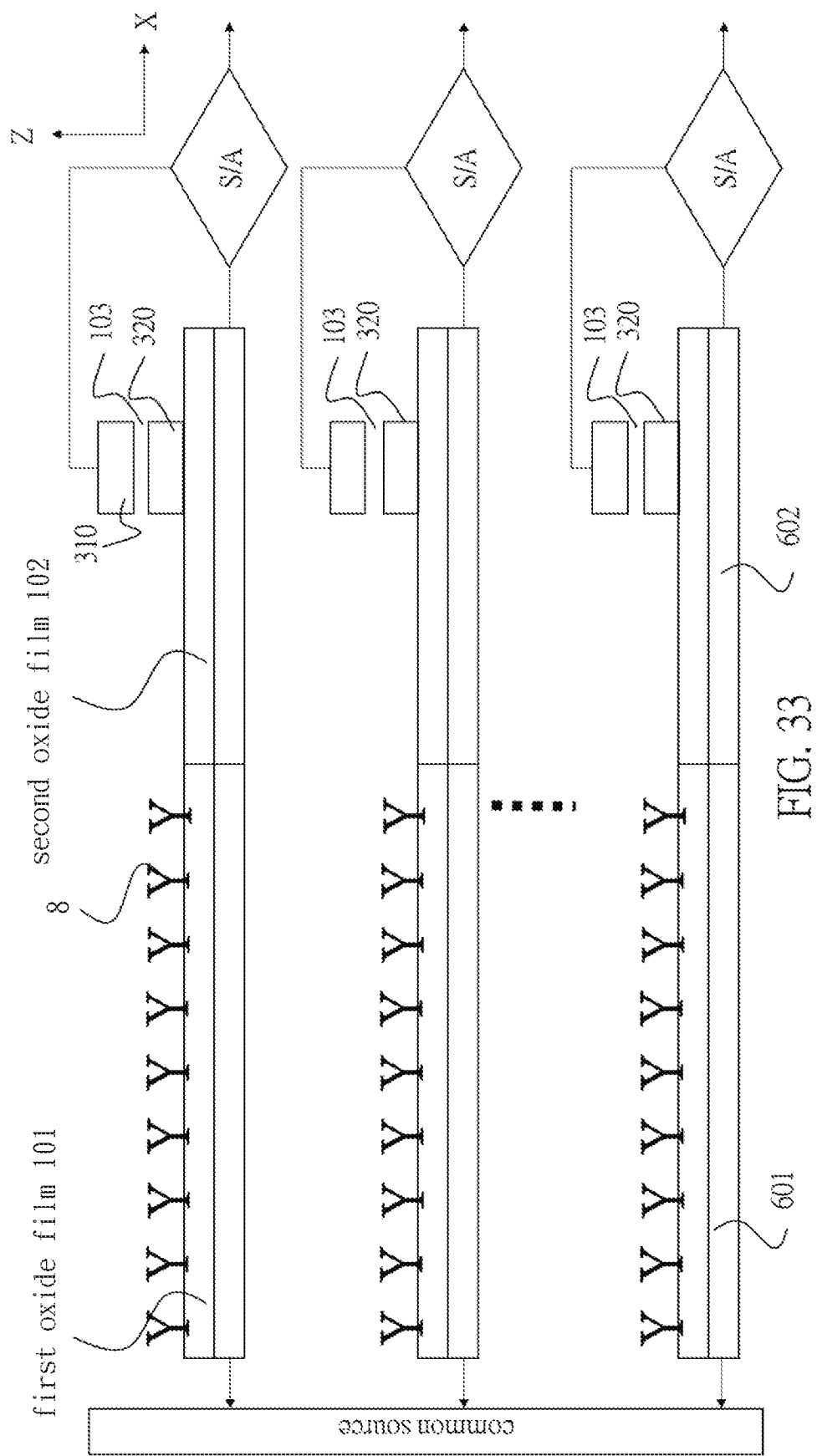
FIG. 33 shows a plurality of conducting wires connected to the plurality of sense-amplifiers, respectively.

In FIG. 33, there is a plurality of conducting wires comprising the above-mentioned components (including the non-volatile memory type transistors). Note that the plurality of first conducting wires 601 is connected to the common source. On the other hand, the plurality of second conducting wires 602 is independently and respectively connected to the plurality of sense-amplifiers. Thus, it is possible to individually control the resistivity of the conducting wires 6 such that all the conducting wires 6 may have same resistivity with a controllable error in FIG. 33, even though the first conducting wires 601 have various resistivities. If the first conducting wire under sensing is snapped or its resistivity is higher than a predetermined limit (i.e., anomalously high), the first conductive wire may be deemed to have a wire-error. The threshold voltage of a non-volatile memory connecting to the first conductive wire having such a wire-error may increase to disconnect this first conductive wire from the corresponding sense-amplifier. This is the data-thinning process that is executed before exposing the semiconductor biosensor into an electrolyte solution under diagnosis. Subsequently, it can be proceeded to tune the resistivity of the plurality of second conductive wires 602 without wire-errors by independently fine-tuning the threshold voltages of those second conductive wires after the data-mining process. This is indispensable to improve the precision of biosensing and the LoD.

Figure 34:
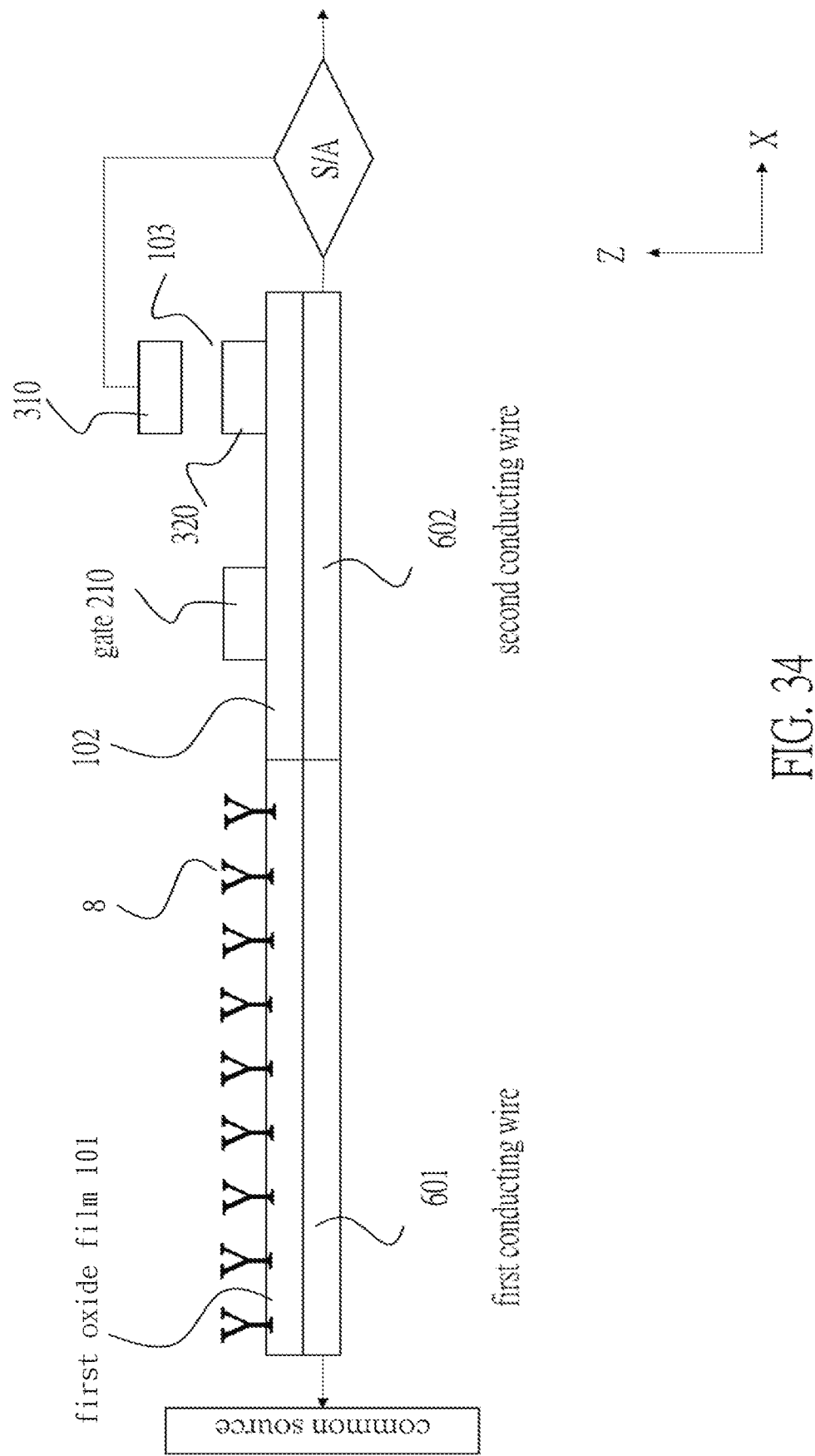
FIG. 34 shows a drain select gate and a non-volatile memory type transistor on the same second conducting wire.
Figure 35:
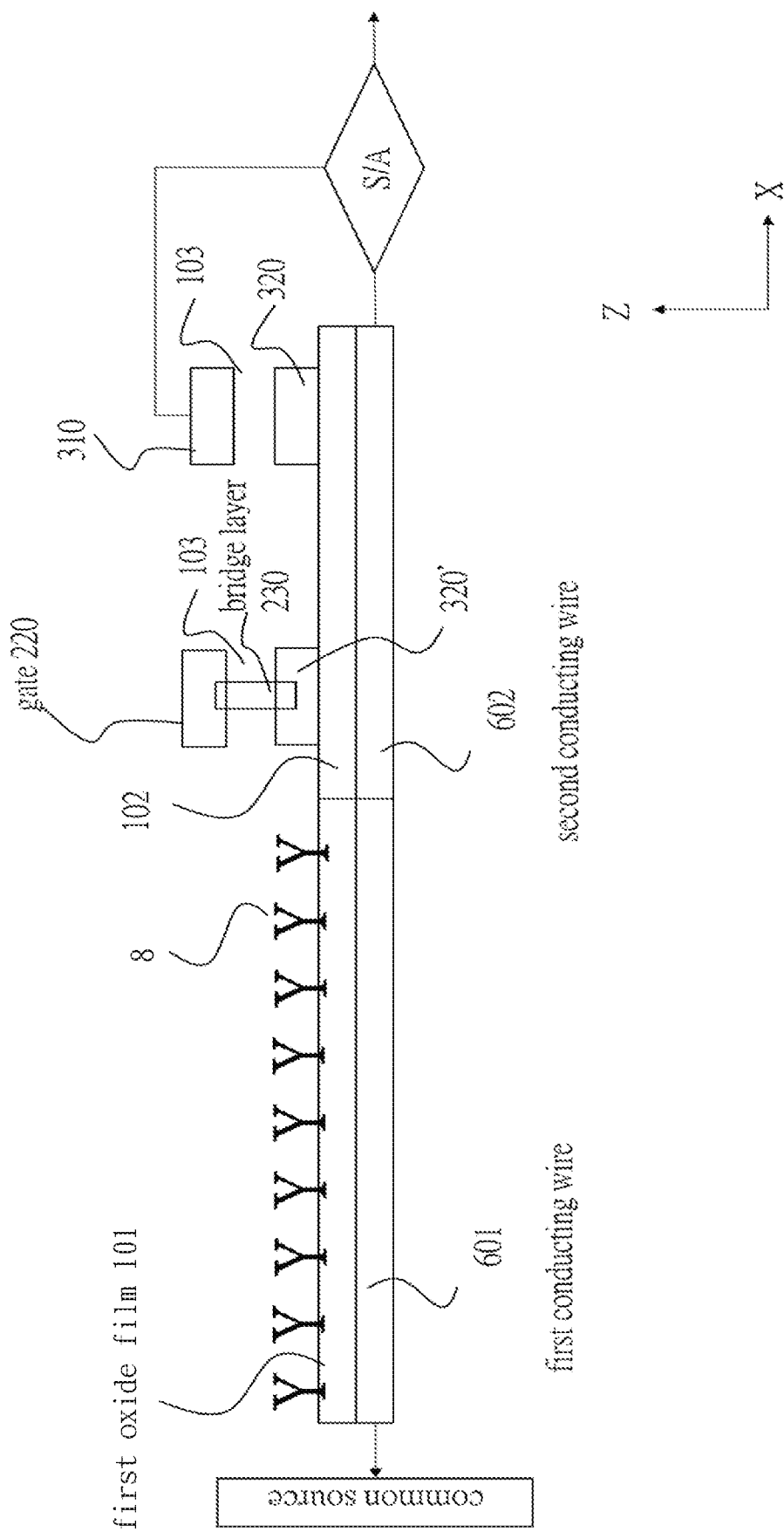
FIG. 35 shows a non-floating gate structure of the non-volatile memory type transistor.

As illustrated in FIG. 34, there can be a drain select gate 210 and a non-volatile memory type transistor on the same second conducting wire. As illustrated in FIG. 35, a gate 210 can be replaced with gate 220 having a bridge layer 230 in a third oxide film above a gate 320' formed on the second oxide film. Since this gate 320' is connected to the control gate 220 by the bridge layer, such that the gate 220, the bridge layer 230 and the gate 320' can form a gate connected to an electrode. In this regard, the gate as formed is no longer a floating gate. The gate 220 can serve as a drain select gate. However, the fabrication of gate 320' and the floating gate 320 may be carried out by a common process.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A semiconductor biosensor comprising:
   a central reaction unit of an inspection equipment, with the central reaction unit configured to be embedded into a semiconductor chip and exposed into a solution dissociating a plurality of targets, wherein the plurality of targets moves in the solution; and
   with the central reaction unit comprising:
   a plurality of first conducting wires;
   a plurality of second conducting wires;
   a common electrode source, wherein an end of each of the plurality of first conducting wires is connected to the common electrode source, and wherein another end of each of the plurality of first conducting wires is connected to an end of a respective one of the plurality of second conducting wires;
   a plurality of sense-amplifiers, wherein each of the plurality of sense-amplifiers is electrically connected to another end of the respective one of the plurality of second conducting wires;
   a plurality of non-volatile memory type transistors respectively formed on the plurality of second conducting wires, wherein each of the plurality of non-volatile memory type transistors comprises a control gate connecting to a corresponding one of the plurality of sense-amplifiers, a third oxide film, a floating gate, and a second oxide film formed below the floating gate and on a corresponding one of the plurality of second conducting wires;
   a first oxide film wrapping or covering the plurality of first conducting wires, wherein a plurality of receptors is fixed on a surface of the first oxide film but not on a surface of the second oxide film, wherein a portion of the plurality of targets couples with a portion of the plurality of receptors to form a plurality of composite bodies;
   wherein the plurality of first conducting wires, the first oxide film and the plurality of receptors jointly delimit a first part of the central reaction unit, wherein the plurality of second conducting wires and the plurality of non-volatile memory type transistors jointly delimit a second part of the central reaction unit, and wherein none of the plurality of second conducting wires and none of the plurality of non-volatile memory type transistors are within the first part,
   wherein the plurality of sense-amplifiers is configured to detect a change in a current signal based on charges of the plurality of composite bodies,
   wherein an improving factor ε of a limit of detection (LOD) of the plurality of sense-amplifiers is defined as:

$$\varepsilon \cong 1 - \frac{m}{M},$$

wherein M is a total number of the plurality of sense-amplifiers, and wherein m is a sum of a number of the plurality of sense-amplifiers which detects one of the plurality of composite bodies and a number of the plurality of sense-amplifiers which are contaminated with noise,
   wherein an improved limit of detection (LOD) of the plurality of sense-amplifiers is defined as:

Improved LOD=(1−ε)×LOD=m/M×LOD, and wherein the semiconductor biosensor is configured to adjust the improving factor ε of the plurality of sense-amplifiers to obtain the improved limit of detection by tuning M and m.

2. The semiconductor biosensor as claimed in claim 1, wherein the central reaction unit further comprises a plurality of drain select gate transistors respectively connected between the plurality of first conducting wires and the plurality of non-volatile memory type transistors.

3. A control method comprising:
   providing the semiconductor biosensor as claimed in claim 1;
   initializing the semiconductor biosensor by independently sensing output signals from the plurality of second conducting wires by the plurality of sense-amplifiers while a read voltage is applied to the control gates, and then testing the plurality of first conducting wires for wire-errors, and wherein a portion of the plurality of first conducting wires with anomalously high resistance or which is snapped is regarded as first conducting wires having said wire-errors;

data-thinning the semiconductor biosensor by selectively applying a program voltage to program one or more of the plurality of non-volatile memory type transistors respectively connected to one or more of the plurality of first conducting wires having said wire-errors to electrically disconnect each of the one or more of the plurality of first conducting wires having said wire-errors from a respective one of the plurality of sense-amplifiers;

exposing the semiconductor biosensor into the solution dissociating the plurality of targets, wherein the plurality of targets moves in the solution; and detecting a change in the current signal output from one of the plurality of first conducting wires without said wire-errors based on the charges of the plurality of composite bodies.

4. The control method as claimed in claim 3, further comprising selectively tuning a threshold voltage of one of the plurality of non-volatile memory type transistors connecting to the one of the plurality of first conducting wires without said wire-errors after said data-thinning by applying a tuning voltage to the control gate of the respective one of the plurality of non-volatile memory type transistors and before exposing the semiconductor biosensor into the solution.

5. The control method as claimed in claim 3, wherein testing the plurality of first conducting wires for said wire-errors comprises:

locating one or more of the plurality of first conducting wires with no sensible electric current according to the output signals sensed by the plurality of sense-amplifiers; and regarding the one or more of the plurality of first conducting wires with no sensible current as the portion of the plurality of first conducting wires with anomalously high resistance or which is snapped.

6. A control method comprising:

providing the semiconductor biosensor as claimed in claim 2;

initializing the semiconductor biosensor by independently sensing output signals from the plurality of first conducting wires by the plurality of sense-amplifiers, and then testing the plurality of first conducting wires for wire-errors, wherein a portion of the plurality of first conducting wires with anomalously high resistance or which is snapped is regarded as first conducting wires having said wire-errors;

data-thinning the semiconductor biosensor by selectively applying a program voltage to program one or more of the plurality of non-volatile memory type transistors respectively connected to one or more of the plurality of first conducting wires having said wire-errors;

exposing the semiconductor biosensor into the solution dissociating the plurality of targets, wherein the plurality of targets moves in the solution; and detecting a change in the current signal based on the charges of the plurality of composite bodies.

7. The control method as claimed in claim 6, further comprising selectively tuning a threshold voltage of one of the plurality of non-volatile memory type transistors connecting to the one of the plurality of first conducting wires without said wire-errors after said data-thinning by applying a tuning voltage to the control gate of the respective one of the plurality of non-volatile memory type transistors and before exposing the semiconductor biosensor into the solution.

8. The control method as claimed in claim 6, wherein testing the plurality of first conducting wires for said wire-errors comprises:

locating one or more of the plurality of first conducting wires with no sensible electric current according to the output signals sensed by the plurality of sense-amplifiers; and regarding the one or more of the plurality of first conducting wires with no sensible current as the portion of the plurality of first conducting wires with anomalous high resistance or which snapped.

* * * * *